United States Patent [19]
Barbas et al.

[11] Patent Number: 5,679,548
[45] Date of Patent: Oct. 21, 1997

[54] METHODS FOR PRODUCING POLYPEPTIDE METAL BINDING SITES AND COMPOSITIONS THEREOF

[75] Inventors: Carlos F. Barbas; Jonathan Rosenblum, both of San Diego; Richard A. Lerner, La Jolla, all of Calif.

[73] Assignee: The Scripps Research Institute, La Jolla, Calif.

[21] Appl. No.: 77,797

[22] Filed: Jun. 14, 1993

Related U.S. Application Data

[63] Continuation of Ser. No. 12,566, Feb. 2, 1993, abandoned.

[51] Int. Cl.[6] .................... C12N 15/13; C07K 16/00; A61K 39/395
[52] U.S. Cl. ................ 435/69.6; 435/70.21; 435/172.1; 435/188.5; 536/25.53; 536/24.3; 530/387.1; 530/400; 514/6; 930/25
[58] Field of Search .................. 435/69.6, 172.1, 435/188.5; 536/24.3; 530/400; 514/6; 930/25

[56] References Cited

PUBLICATIONS

Barbas et al. PNAS 89 p. 4457–4461 1992.
Roberts et al. PNAS 87 pp. 6654–6658 1990.
Iverson et al. Science vol. 249:659 1990.
Stansfield et al. Tibtech 12: 275 1994.

*Primary Examiner*—Lila Feisee
*Assistant Examiner*—John Lucas
*Attorney, Agent, or Firm*—Thomas Fitting; Emily Holmes

[57] ABSTRACT

The present invention describes methods for producing metal binding sites on polypeptides, and particularly for producing metal binding sites within the CDR regions of immunoglobulin heavy or light chains that are displayed on the surface of filamentous phage particles. The invention also describes oligonucleotides useful for preparing the metal binding sites, and human monoclonal antibodies produced by the present methods.

18 Claims, 2 Drawing Sheets

METHODS FOR PRODUCING POLYPEPTIDE METAL BINDING SITES AND COMPOSITIONS THEREOF

CROSS-REFERENCE TO RELATED APPLICATION

This application is a continuation application of Ser. No. 08/012,566, filed Feb. 2, 1993 now abandoned, the disclosures of which are hereby incorporated by reference.

TECHNICAL FIELD

The present invention relates generally to the field of protein biochemistry and immunology, and relates specifically to polypeptides containing metal binding sites and the methods for producing them.

BACKGROUND

Protein interactions with other molecules is basic to biochemistry. Protein interactions include receptor-ligand interactions, antibody-antigen interactions, cell-cell contact and pathogen interactions with target tissues. Protein interactions can involve contact with other proteins, with carbohydrates, oligosaccharides, lipids, metal ions and the like materials.

The basic unit of protein interaction is the region of the protein involved in contact and recognition, and is referred to as the binding site.

There is an increasing need to find new molecules which can effectively modulate a wide range of biological processes, for applications in medicine and agriculture. Thus, there is a need for systematic and rapid development of binding sites on proteins for use in the construction of protein binding site analogs and antagonists, proteins with improved or altered binding specificities and the attendant altered function associated with the altered specificity, and antibodies with unique antigen specificities.

Proteins containing metal ion binding sites are especially biologically relevant in that they provide both diagnostic and therapeutic functions. Metalloproteins as a class are proteins having a metal ion complexed with the protein molecule at the protein's metal binding site. The metal ion contributes to the protein's function by a variety of chemical mechanisms including stabilizing protein structure, facilitating electron transfer in oxidation or reduction reactions, and the like.

The stereochemistry of metal ion complex structure in association with protein has been extensively characterized. Studies of known metalloproteins have resulted in the characterization of many metal ions that participate in metal-protein complexes, which help to identify the nature of the metal-protein complex. Three dimensional structures of metalloproteins based on X-ray crystallographic data are available for numerous metalloproteins and provide further insight into the nature of the metal-protein complex.

Numerous strategies have been developed for preparing proteins having new binding specificities besides the conventional technique of random screening of natural products. These approaches generally involve the synthetic production of large numbers of random molecules followed by some selection procedure to identify the molecule of interest. For example, epitope libraries have been developed using random polypeptides displayed on the surface of filamentous phage particles. The library is made by synthesizing a repertoire of random oligonucleotides to generate all combinations, followed by their insertion into a phage vector. Each of the sequences is separately cloned and expressed in phage, and the relevant expressed peptide can be selected by finding those phage that bind to the particular target. The phages recovered in this way can be amplified and the selection repeated. The sequence of the peptide is decoded by sequencing the DNA. See for example Cwirla et al., *Proc. Natl. Acad. Sci., USA*, 87:6378–6382 (1990); Scott et al., *Science*, 249:386–390 (1990); and Devlin et al., *Science*, 249:404–406 (1990).

Another approach involves large arrays of peptides that are synthesized in parallel and screened with acceptor molecules labelled with fluorescent or other reporter groups. The sequence of any effective peptide can be decoded from its address in the array. See for example Geysen et al., *Proc. Natl. Acad. Sci., USA*, 81:3998–4002 (1984); Maeji et al., *J. Immunol. Met.*, 146:83–90 (1992); and Fodor et al., *Science*, 251:767–775 (1991).

In another approach, Lam et al., *Nature*, 354:82–84 (1991) describes combinatorial libraries of peptides that are synthesized on resin beads such that each resin bead contains about 20 pmoles of the same peptide. The beads are screened with labeled acceptor molecules and those with bound acceptor are searched for by visual inspection, physically removed, and the peptide identified by direct sequence analysis. In principle, this method could be used with other chemical entities but it requires sensitive methods for sequence determination.

A different method of solving the problem of identification in a combinatorial peptide library is used by Houghten et al., *Nature*, 354:84–86 (1991). For hexapeptides of the 20 natural amino acids, 400 separate libraries are synthesized, each with the first two amino acids fixed and the remaining four positions occupied by all possible combinations. An assay, based on competition for binding or other activity, is then used to find the library with an active peptide. Twenty new libraries are then synthesized and assayed to determine the effective amino acid in the third position, and the process is reiterated in this fashion until the active hexapeptide is defined. This is analogous to the method used in searching a dictionary; the peptide is decoded by construction using a series of sieves or buckets and this makes the search logarithmic.

Large libraries of wholly or partially synthetic antibody combining sites, or paratopes, have been constructed utilizing filamentous phage display vectors, referred to as phagemids, yielding large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries. Kang et al., *Proc. Natl. Acad. Sci., USA*, 88:4363–4366 (1991). Combinatorial libraries of antibodies have been produced using both the cpVIII membrane anchor (Kang et al., supra) and the cpIII membrane anchor. Barbas et al., *Proc. Natl. Acad. Sci., USA*, 88:7978–7982 (1991).

The diversity of a filamentous phage-based combinatorial antibody library can be increased by shuffling of the heavy and light chain genes (Kang et al., *Proc. Natl. Acad. Sci., USA*, 88:11120–11123, (1991), by altering the complementarity determining region 3 (CDR3) of the cloned heavy chain genes of the library (Barbas et al., *Proc. Natl. Acad. Sci., USA*, 89:4457–4461, 1992), and by introducing random mutations into the library by error-prone polymerase chain reactions (PCR) (Gram et al., *Proc. Natl. Acad. Sci., USA*, 89:3576–3580, 1992).

Mutagenesis of proteins has been utilized to alter the function, and in some cases the binding specificity, of a protein. Typically, the mutagenesis is site-directed, and therefore laborious depending on the systematic choice of mutation to induce in the protein. See, for example Corey et al., *J. Amer. Chem. Soc.*, 114:1784–1790 (1992), in which rat trypsins were modified by site-directed mutagenesis. Partial randomization of selected codons in the thymidine kinase (TK) gene was used as a mutagenesis procedure to develop variant TK proteins. Munir et al., *J. Biol. Chem.*, 267:6584–6589 (1992).

In one approach, Roberts et al., *Gene*, 121:9–15 (1992), described the point mutation of a protease inhibitor (BPTI) as a fusion protein with gene III of a phagemid, and demonstrated a change in binding specificity such that the mutant binds human neutrophil elastase rather than trypsin. Similarly, Roberts et al., *Proc. Natl. Acad. Sci., USA*, 89:2429–2433 (1992), produced by mutagenesis, a library of phage displaying mutant trypsin inhibitor, and isolated variant enzymes with increased affinity.

While mutagenesis has not been utilized to create metal binding sites in proteins, the sequence encoding a metal binding protein has been engineered into an antibody-encoding construct, the expression of which forms a chimeric protein as described by Das et al., *Proc. Natl. Acad. Sci., USA*, 89:9749–7953 (1992) and Sawyer et al., *Proc. Natl. Acad. Sci., USA*, 89:0754–9758 (1992). Freeman et al., *Adv. Protein Chem.*, 22:257–424 (1967), has described the preparation of synthetic metal binding sites on polypeptides. In addition, nonapeptide sequences that were inserted into an exposed portion of the lam B protein which allowed for the selection of *E. coli* that adhered to the iron oxide, magnetite, as described by Brown, *Proc. Natl. Acad. Sci., USA*, 89:8651–8655 (1992). Naturally occurring bacteria that accumulate magnetite have also been identified as described by Matsunag, *Trends in Biotechnology*, 9: 91–95 (1991). Alterations of existing metalloproteins have been reported in which amino acid residues that participate in the metal-protein complex were substituted, resulting in changes in the apoprotein's metal ion specificity and in the binding constant for the metal ion. However, no protein structure has been engineered to allow for the ability to actively select for a metal binding site in a protein.

BRIEF DESCRIPTION OF THE INVENTION

Methods have now been discovered using the phagemid vectors to produce metal binding sites capable of binding (interacting with) any of a large variety of target metals.

Thus, in one embodiment, the invention describes a method for producing in a polypeptide a binding site capable of binding a preselected agent comprising introducing a nucleotide sequence that codes for an amino acid residue sequence defining the binding site into a CDR of a nucleic acid comprising an immunoglobulin heavy or light chain gene.

In particular, the invention describes a method for producing a metal binding site in a polypeptide capable of binding a preselected metal. An oligonucleotide useful as a primer is used in a primer extension reaction for producing a metal binding site in a polypeptide coded for by a hybrid immunoglobulin heavy or light chain gene by amplifying the CDR of a nucleic acid of the immunoglobulin gene. The oligonucleotide has 5' and 3' termini and comprises:

a) a nucleotide sequence of about 5 to 50 nucleotides in length at the 3' termini capable of hybridizing to a first framework region of the immunoglobulin gene;

b) a nucleotide sequence of about 5 to 50 nucleotides in length at the 5' termini capable of hybridizing to a second framework region of the immunoglobulin gene; and c) a nucleotide sequence between said 5' and 3' termini according to the formula:

[NNS]$_a$, where a is a whole integer from 3 to 50, N is independently any nucleotide, S is cytosine (C) or guanosine (G) or analogs thereof, and wherein said 5' and 3' terminal nucleotide sequences have a length of about 6 to 50 nucleotides in length, and sequences complementary thereto.

The choice of framework regions depends on the CDR into which the binding site is to be inserted. Thus, for example, for an insertion into CDR3, the 3' and 5' regions of the oligonucleotides are selected as to be complementary in nucleotide sequence to the coding strand defining FR4 and FR3 that flank CDR3, respectively, where the oligonucleotide is to be complementary to the noncoding (anti-sense) strand of the template DNA.

A preferred and exemplary CDR for insertion of a binding site is the CDR3 of immunoglobulin heavy chain. Particularly preferred is the immunoglobulin heavy chain display protein present in the vectors pC3AP313 and p7EII, described herein.

Additionally contemplated for use in this invention is the complementary nucleotide sequence of the preferred oligonucleotide formulation and identified sequences. Specifically, the complementary oligonucleotide has 5' and 3' termini between which is the nucleotide formulation [SNN]$_a$. This alternative embodiment of a complementary oligonucleotide thus hybridizes to the coding (sense) strand of the template DNA.

In another embodiment, the invention contemplates a method for producing in a polypeptide a metal binding site capable of binding a preselected metal wherein the binding site is in an immunoglobulin where two amino acid residues of the gene are retained. An oligonucleotide useful as a primer is used in a primer extension reaction for producing a metal binding site in a polypeptide encoded by a hybrid immunoglobulin heavy or light chain gene by amplifying the CDR of a nucleic acid of the immunoglobulin heavy or light chain gene. The oligonucleotide has 5' and 3' termini and comprises:

a) a nucleotide sequence of about 5 to 50 nucleotides in length at the 3' termini capable of hybridizing to a first framework region of the immunoglobulin gene;

b) a nucleotide sequence of about 5 to 50 nucleotides in length at the 5' termini capable of hybridizing to a second framework region of the immunoglobulin gene; and c) a nucleotide sequence between said 5'0 and 3' termini according to the formula:

-X-[NNK]$_a$-X-[NNK]-X-, where a is a whole integer from 3 to 50, X is a trinucleotide encoding a native amino acid residue coded by the immunoglobulin gene, N is independently any nucleotide, K is guanosine (G) or thymine (T) or analogs thereof, wherein said internal X is one nucleotide triplet encoding one immunoglobulin gene amino acid residue and wherein said 5' and 3' terminal nucleotide sequences have a length of about 6 to 50 nucleotides in length, and sequences complementary thereto.

The methods of this invention further comprises the steps of:

a) isolating the amplified CDR to form mutagenized immunoglobulin genes;

b) expressing the isolated mutagenized immunoglobulin genes; and c) selecting species of the expressed mutagenized immunoglobulin genes for the ability to bind a preselected metal ion-containing molecule.

Contemplated for use in methods for producing a metal binding site is a preselected metal ion-containing molecule is selected from the group consisting of magnetite, copper (II), zinc(II), lead(II), cerium(III), and iron(III).

This invention describes human monoclonal antibodies produced according to the methods capable of immunoreacting with magnetite, copper(II), zinc(II), lead(II), cerium (III), and iron(III), wherein the monoclonal antibody has the binding specificity of a monoclonal antibody comprising a heavy chain immunoglobulin variable region amino acid residue sequence.

In another embodiment, the invention contemplates pharmaceutical compositions comprising at least one dose of an immunotherapeutically effective amount of the human monoclonal antibodies containing metal binding sites.

Also described is a DNA expression vector capable of expressing a phagemid immunoglobulin display protein comprising a polynucleotide sequence that codes an immunoglobulin heavy chain polypeptide that includes in the CDR3 portion of the heavy chain a binding site able to bind a preselected target molecule.

A major advantage of the methods of the invention derives from the fact that new proteins having new metal binding specificities can be rapidly developed for use in a variety of ways.

BRIEF DESCRIPTION OF THE DRAWINGS

In the drawings forming a portion of this disclosure.

DETAILED DESCRIPTION OF THE INVENTION

A. Definitions

Amino Acid Residue

Figure 1:
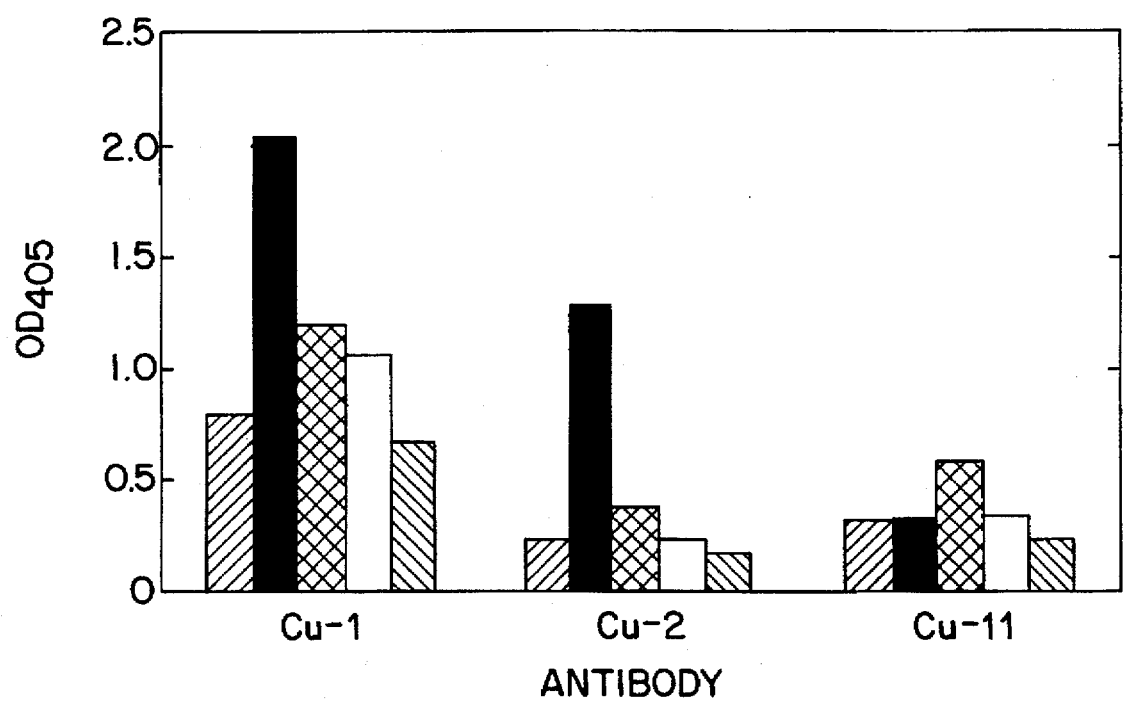
FIG. 1 is a graph of the comparison of binding specificities of three purified clones that were selected for Cu(II) binding. Specificity was examined by ELISA. Antigens were (from left to right) Mg(II) BSA-IDA, Ni(II) BSA-IDA, Cu(II) BSA-IDA, Zn(II) BSA-IDA, and BSA-IDA (no metal).
Figure 2A:
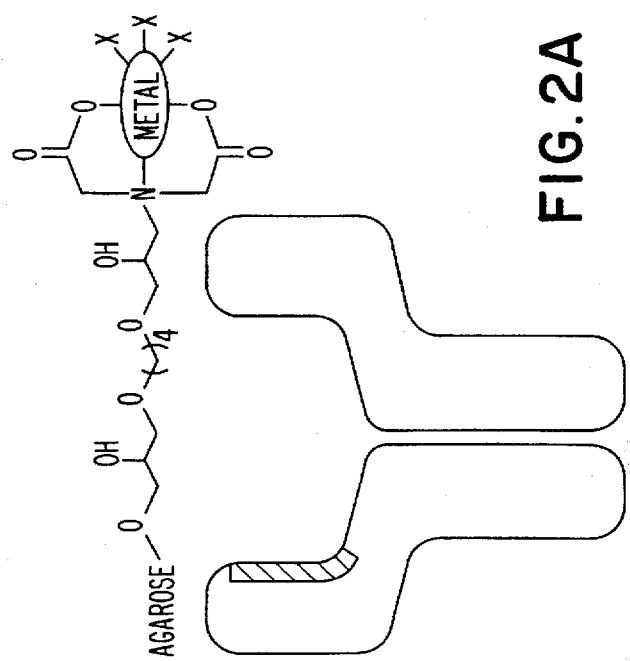
FIG. 2A depicts an antibody binding site formed by the dimerization of heavy and light chains. The hatched region indicates an antibody CDR which has been targeted for mutagenesis. The resulting library of antibodies are then selected to bind the metal-iminodiacetic acid complex shown at the top of panel A where X designates a vacant ($H_2O$) coordination site. The antibodies which result are shown in FIG. 2B where the vacant X sites of the complex shown in panel A are substituted for His ligands in this example. The coordination sites formerly occupied by IDA are now vacant(X).
Figure 2B:
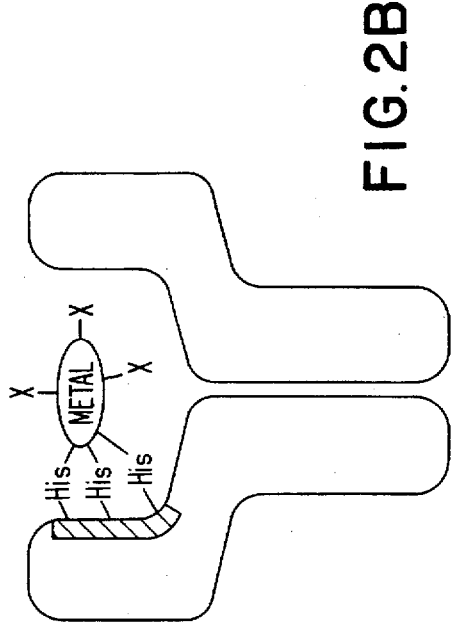
FIG. 2 is a schematic representation of an iterative strategy for selection of catalytic synthetic antibodies.
FIG. 2C depicts the diversification of the metal binding antibodies by mutagenesis of another CDR or chain shuffling. The resulting sublibrary is then selected for binding to an appropriately designed hapten to produce catalytic metalloantibodies shown in FIG. 2D to bind both metal and hapten.
Figure 2C:
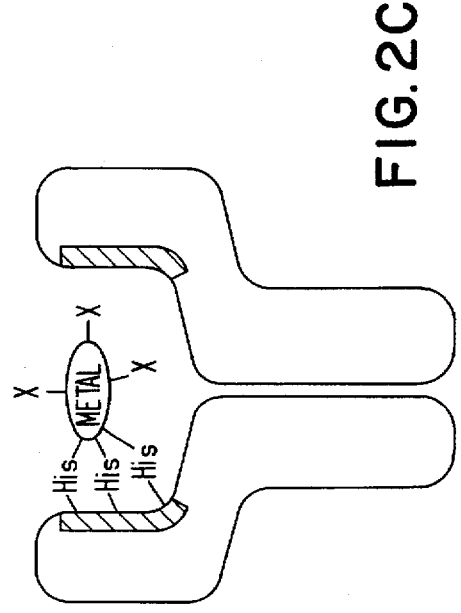
Figure 2D:
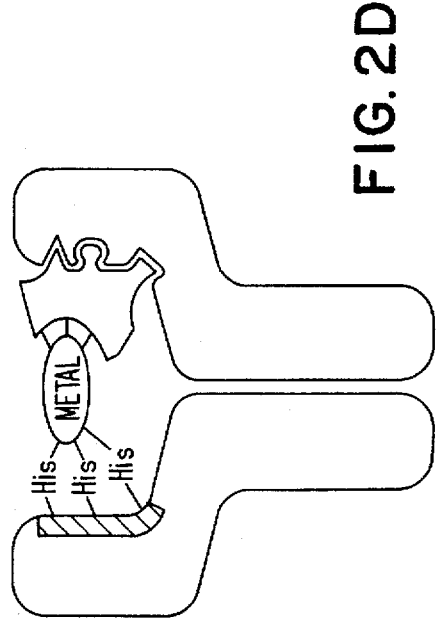

An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 CFR §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Recombinant DNA (rDNA) Molecule

A DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector

A rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) from mRNAs produced using reverse transcriptase.

Receptor

A receptor is a molecule, such as a protein, glycoprotein and the like, that can specifically (non-randomly) bind to another molecule.

Antibody

The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site

An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody

A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Fusion Polypeptide A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Upstream

In the direction opposite to the direction of DNA transcription, and therefore going from 5' to 3' on the noncodingstrand, or 3' to 5' on the mRNA.

Downstream

Further along a DNA sequence in the direction of sequence transcription or read out, that is traveling in a 3'- to 5'-direction along the noncodingstrand of the DNA or 5'- to 3'-direction along the RNA transcript.

Cistron

A sequence of nucleotides in a DNA molecule coding for an amino acid residue sequence and including upstream and downstream DNA expression control elements.

Leader Polypeptide

A short length of amino acid sequence at the amino end of a polypeptide, which carries or directs the polypeptide through the inner membrane and so ensures its eventual secretion into the periplasmic space and perhaps beyond. The leader sequence peptide is commonly removed before the polypeptide becomes active.

Reading Frame

A particular sequence of contiguous nucleotide triplets (codons) employed in translation. The reading frame depends on the location of the translation initiation codon.

B. Structure of a Polypeptide Metal Binding Site

A binding site, and more particularly a metal binding site as described in more detail below, is any region of a protein or polypeptide that participates in protein—target molecule interactions, and therefore the identification of the primary sequence of a binding site is important in constructing a functional binding site-containing molecule.

The display of a binding site on a filamentous phage is essential to the present invention as it provides the ability to screen for capacity of the displayed binding site to bind to a preselected target molecule. Display is described in more detail but generally involves the preparation of a fusion protein containing a membrane anchor of the filamentous phage gene III or gene VIII protein fused to the polypeptide to be displayed that forms a binding site to be tested. Peptide display vectors using hexapeptides have been generally described before by Cwirla et al., *Proc. Natl. Acad. Sci., USA*, 87:6378–6382 (1990); Scott et al., *Science*, 249:386–390 (1990); and Devlin et al., *Science*, 249:404–406 (1990).

According to the present methods, the use of an antibody heavy or light chain as the display support structure on a recombinant filamentous phage, or phagemid, is particularly preferred. The use of an antibody support for a binding site provides a "scaffold" for presenting a conformationally constrained polypeptide to preselected binding conditions. In this embodiment, the CDR of an immunoglobulin heavy or light chain is randomly mutated to result in a metal binding site that is presented on a phagemid, and the phagemid can then be screened for binding to a preselected target molecule.

The introduction of a binding site onto a display phagemid involves the use of degenerate oligonucleotides to mutate an immunoglobulin CDR region, followed by a selection step. The methods of this invention result in mutated antibody populations that have metal binding sites for binding to preselected metal cations (also referred to as metals), as described herein. The degenerate oligonucleotides contain regions of degeneracy to produce a library of different binding site structures within a CDR of a variable region in a heavy or light chain.

The region of a preselected phagemid display protein gene is first amplified by a primer extension reaction using a primer oligonucleotide having (1) regions complementary to the display protein gene, and (2) regions of degeneracy that introduce the variability into the resulting pool of display proteins for selecting metal binding specificities.

After the primer extension reaction, which may be accomplished in a variety of modes including polymerase chain reaction (PCR), crossover PCR, and the like, the resulting population of display protein genes are expressed in phagemids to form a population of phagemid particles having the display proteins with binding sites on the particle surface. The population of particles are then screened for the presence of particles containing a metal binding site that binds to a preselected metal target molecule.

1. Metal Binding Site Polypeptides

A metal binding site, also referred to as a metal cation binding site, can be any polypeptide sequence, typically about 3 to 50 amino acid residues in length, that defines a region of a protein or polypeptide that selectively interacts with another molecule or family of related molecules, referred to as target molecules that contain a metal moiety.

As is known in protein biochemistry, proteins, and therefore binding sites as defined herein, can interact with a wide diversity of molecules including other proteins, in the form of receptors, tissue structures, and soluble proteins, polypeptides including degraded proteins, polypeptide hormones and ligands, lipid, oligosaccharides and carbohydrates, nucleic acids and inorganic molecules such as metal ions. The latter is the preferred target molecule for use in selecting metal binding site-containing polypeptides of this invention.

As shown herein and by other work in the field, the amino acid residue sequence of a binding site can tolerate some degree of variability and still retain a degree of capacity to bind the target molecule. Furthermore, changes in the sequence can result in changes in the binding specificity and in the binding constant between a preselected target molecule and the binding site.

The metal cation binding sites of this invention are presented in the context of an immunoglobulin that represents a large family of molecules that include several types of molecules, such as IgD, IgG, IgA, IgM and IgE. An immunoglobulin is typically comprised of two heavy (H) and two light (L) chains with both a variable (V) and constant (C) region present on each chain. Several different regions of an immunoglobulin contain conserved sequences on the basis of comparative studies of known sequences of heavy or light chains.

Extensive amino acid and nucleic acid sequence data displaying exemplary conserved sequences have been compiled for immunoglobulin molecules by Kabat et al., in *Sequences of Proteins of Immunological Interest*, 4th Ed., National Institutes of Health, Bethesda, Md. (1987).

Present understanding of the sites of an antibody molecule responsible for antigen-antibody binding indicates that part of the antibody combining site is formed by heavy chain hypervariable regions, and part of the combining site is formed by the light chain hypervariable regions. See for example, Getzoff et al., *Adv. Immunol.*, 43:1–98 (1988). Six loops of polypeptide comprise the hypervariable regions; three loops from the variable region of the light chain ($V_L$) and three loops from the variable region of the heavy chain ($V_H$), denoted L1, L2, L3 and H1, H2, H3 respectively. See for example, Chothia et al., *Nature*, 342:877–883 (1989). The hypervariable regions are also known as complementarity determining regions, or CDRs.

Comparative studies of the known three dimensional structure of numerous antibody molecules have identified that each hypervariable region adopts one of a few main chain conformations or canonical structures. Using sequence homologies, the amino acid residue sequence of a heavy or light chain are aligned with the sequence of a known immunoglobulin heavy or light chain structure, respectively, the hypervariable region loops and specific amino acid residue positions within the loops, of the heavy or light chain can be reproducibly identified.

Thus, for example, a L1, L2 or L3 loop structure (CDR L1, CDR L2 or CDR L3) can be reproducibly identified solely on the basis of sequence homologies to other immunoglobulin light chains, thereby locating the position of critical residue positions within the loop structure. Due to the existence of variation in the chain length for a particular immunoglobulin light chain, amino acid residue position numbers are referred to herein by a numbering scheme that is based on alignments using homologous sequences as described by Kabat et al., in *Sequences of Proteins of Immunological Interest*, 4th Ed., U.S. Department of Health and Human Services, National Institute of Health, Bethesda, Md. (1987). Specific residue number reference to the amino acid residue positions for particular residues, therefore, will be cited herein as "Kabat position number" or "Kabat amino acid residue position number" to connote a reproducibly identifiable residue position on a recognized CDR loop structure. Wherever position numbers are given, they refer to Kabat positions.

The V region of any immunoglobulin heavy or light chain molecule having the identifiable loop structures are useful in the present invention to produce a metal cation binding site.

A metal cation binding site is formed by the reproducible folding of a V region into its characteristic folded structure engineered to contain specific contact amino acid residues. The metal binding site is formed by the geometric positioning of three metal ligands (contact sites) provided by the side chain residues of three contact amino acid residues to form coordinating ligands for complexing a metal cation. Thus, the contact amino acid residues in the CDR amino acid residue sequence of an immunoglobulin V region defines a metal binding site.

The structure and stereochemistry of protein-metal interactions in metalloproteins is generally well understood. See for example, Freeman et al., *Adv. Protein Chem.*, 22:257–424 (1967); Kannan et al., *Annals. NY Acad. Sci.*, 429:49 (1984); and Tainer et al., *J. Mol. Biol.*, 160:181–217 (1982).

In the conventionally known models of metal ligand binding, the metal ligands (contact sites) for binding a metal cation to a metal binding site in a V region are positioned at three locations to provide three ligand contact points typically required for a metal cation coordination complex. Representative coordination complex geometries for the metal ligands can potentially be tetrahedral, square planar or trigonal depending upon the metal cation. However, tetrahedral geometries are preferred. Representative coordination metal complexes of the preferred tetrahedral coordinating geometry are shown by the structure of the zinc(II) complex in the enzyme superoxide dismutase, or the copper (II) complex in carbonic anhydrase. See Tainer et al., *J. Mol. Biol.*, 160:181–217 (1982); and Kannan et al., *Annals. NY Acad. Sci.*, 429:49 (1984). In these referenced examples, although a metal cation presents four potential contact sites, typically three participate in the metal-ligand contact, and the fourth site on the metal cation is free to participate in electron exchanges or sharing with solvent or solute in solution having access to the complexed metal.

In the predicted metal binding contact sites described above, an amino acid residue that occupies one of the three amino acid residue positions to provide a metal ligand contact site in a metal binding site is referred to as a contact amino acid residue. Amino acid residues usually found as contact amino acid residues are known in the art of metalloprotein biochemistry and include histidine, cysteine, methionine, aspartic acid, glutamic acid and the like residues known to provide a ligand for metal cations in metalloproteins.

Metal binding sites of this invention have been prepared in V regions using randomized oligonucleotide sequences to mutate immunoglobulin CDRs, followed by selection of the resulting mutated antibody populations for binding to preselected metal cations, as described herein.

Thus, in one embodiment, a mutagenized CDR has the ability to complex with (bind) a metal cation through ligands (contacts) provided by contact amino acid residues in the polypeptide sequence in the CDR. The contact amino acid residues are presented in a geometry that coordinates the complexation of a metal cation.

The mutagenized CDR contains a sequence of amino acids that results in a site that binds metal cation and is therefore referred to as a metal cation binding site. A metal cation is bound because the randomly mutagenized CDR is capable of forming a coordination complex with the metal cation.

As described further herein, a preferred and exemplary phage display protein is an immunoglobulin heterodimer in which the fusion to a phagemid membrane anchor is through an immunoglobulin heavy chain polypeptide. In addition, a human monoclonal antibody in the form of a soluble Fab fragment can readily be prepared from the phagemid display vector. In this regard, the resulting human monoclonal antibody (Mab), whether a Mab, Fab and the like, produced having, for example, a metal binding site that binds to copper(II) ($Cu^{2+}$) for example is referred to generally as Mab $Cu^{2+}$ to connote the presence of the copper-reactive metal binding site.

Preferred metal cation binding sites shown to bind magnetite ($Fe_3O_4$), also designated Mg, in phagemid display proteins or in soluble forms of the antibodies thereof have been identified by the present methods and have the individual amino acid residue sequences as follows:

| Designation | (SEQ ID NO) | Amino Acid Residue Sequence |
| --- | --- | --- |
| Mg-1 | 1 | SRRSRHHPRMWNGLDV |
| Mg-2 | 2 | GRFKRVRDRWVVIFDF |
| Mg-3 | 3 | GVARSKKMRGLWRLDV |
| Mg-4 | 4 | GLAVRSKRGRFFLFDV |

The underlined amino acid residues in antibodies Mg-1, Mg-3 and Mg-4 highlight the similarities between the phagemid clones and the expressed phagemid display proteins. The underlined amino acid residues in Mg-2 indicates a novel basic region. The RRSRHH- and RSKRGR-containing sequences were each found 3 times with identical sequences at nucleotide level. For all the magnetite-specific binding antibodies, the first and penultimate amino acid residues are fixed as glycine (G) and aspartic acid (D), respectively. Consensus features are apparent in all the magnetite-specific antibodies. The amino terminal portion of all the loops are rich in basic amino acids whereas the carboxy terminus is rich in hydrophobic residues. Three of four clones bear arginine (R) at position 9 and valine (V) at position 16. Two clones have an RSK triplet and one a RSR triplet.

Other preferred metal cation binding sites shown to bind copper(II), designated $Cu^{2+}$, in phagemid display proteins or in soluble forms of the antibodies thereof have been identified by the present methods and have the individual amino acid residue sequences as follows:

| Designation | (SEQ ID NO) | Amino Acid Residue Sequence |
| --- | --- | --- |
| Cu-1 | 5 | GRVHHHSLDV |
| Cu-2 | 6 | SWKHHAHWDV |
| Cu-3 | 7 | GSWDHRGCDG |
| Cu-4 | 8 | GHHMYGGWDH |
| Cu-5 | 9 | GHWGRHSLDT |
| Cu-6 | 10 | GHILHHQLDL |
| Cu-7 | 11 | SSQRLMLGDN |
| Cu-8 | 12 | SHHGHHYLNH |
| Cu-9 | 13 | GKLMMSWCRDTEGCDH |
| Cu-10 | 14 | GDTHRGHLRHHLPHDW |
| Cu-11 | 15 | GWGLWMKPFVWRAWDM |

The copper-reactive antibodies exhibit unique specificity characteristics resulting from the random selection procedure methods of this invention. Interestingly, two of these antibodies, Cu-1 and Cu-2, exhibit a marked preference for nickel (Ni(II)) over all the other metals examined as described in Example 4. These unique binding preferences highlight the diversity which still exists in the metal binding sublibrary obtained by the methods as described herein. Analysis of the sequences of the selected antibodies confirms the success of the selection strategy.

With the Cu(II) chelating sequences, based on the knowledge of characterized copper-containing protein structures, the expected ligands are His, Met, and Cys. A total of 106 positions within the 11 preferred Cu(II)-selected CDRs were randomized with the oligonucleotide having the repeated degenerate formulation NNK in the mutagenesis procedure. Histidine was selected at 26 positions, Met at 6, and Cys at 3. The NNK mix provides each of these residues at only one part in 32 in the unselected library. One clone contains an unpaired Cys residue which is a rare feature in antibody CDRs. Three clones contain a His at the heavy chain CDR3 position 102 which is predicted not to be on the surface of the protein. The two His-rich clones demonstrated a preference for Ni(II) while only the Trp rich clone showed selectivity for Cu(II).

Additionally preferred metal cation binding sites shown to bind zinc(II), designated $Zn^{2+}$, in phagemid display proteins or in soluble forms of the antibodies thereof have been identified by the present methods and have the individual amino acid residue sequences as follows:

| Designation | (SEQ ID NO) | Amino Acid Residue Sequence |
| --- | --- | --- |
| Zn-1 | 16 | SHTHALPLDF |
| Zn-2 | 17 | GRVHHHSLDV |
| Zn-3 | 18 | GQSSGGDTDD |
| Zn-4 | 19 | GQWTPRGDDF |
| Zn-5 | 20 | GRCCPSSCDE |
| Zn-6 | 21 | GPAKHRHRHVGQMHDS |

Further preferred metal cation binding sites shown to bind lead(II), designated $Pb^{2+}$, in phagemid display proteins or in soluble forms of the antibodies thereof have been identified by the present methods and have the individual amino acid residue sequences as follows:

| Designation | (SEQ ID NO) | Amino Acid Residue Sequence |
| --- | --- | --- |
| Pb-1 | 22 | GNLRRKTSDI |
| Pb-2 | 23 | GESDSKREDG |
| Pb-3 | 24 | GGPSLAVGDW |
| Pb-4 | 25 | GPLQHTYPDY |
| Pb-5 | 26 | GWKVTAEDSTEGLFDL |
| Pb-6 | 27 | GTRVWRVCQWNHEEDG |
| Pb-7 | 28 | GEWWCSFAMCPARWDF |
| Pb-8 | 29 | GDTIFGVTMGYYAMDV |

Further preferred metal cation binding sites shown to bind cerium(III) hydroxide, designated $Ce^{3+}$, in phagemid display proteins or in soluble forms of the antibodies thereof have been identified by the present methods and have the individual amino acid residue sequences as follows:

| Designation | (SEQ ID NO) | Amino Acid Residue Sequence |
| --- | --- | --- |
| Ce-1 | 30 | GQVMQELGDA |
| Ce-2 | 31 | GLTEQQLQDG |
| Ce-3 | 32 | GYSYSVSPDA |
| Ce-4 | 33 | GRLGLVMTDE |

-continued

| Designation | (SEQ ID NO) | Amino Acid Residue Sequence |
| --- | --- | --- |
| Ce-5 | 34 | STWPGRQRLGQALSDS |
| Ce-6 | 35 | GYELSWGVDQQEWWDI |
| Ce-7 | 36 | GPVRGLDQSKGVRYDN |
| Ce-8 | 37 | GLSQHIVSETQSSGDL |
| Ce-9 | 38 | GLESLKVLGVQLGGDL |
| Ce-10 | 39 | GNMILGGPGCWSSADI |
| Ce-11 | 40 | GCWNVQRLVVYHPPDG |
| Ce-12 | 41 | GFEVTCSWFGHWGRDS |

Further preferred metal cation binding sites shown to bind iron(III) chloride, designated $Fe^{3+}$, in phagemid display proteins or in soluble forms of the antibodies thereof have been identified by the present methods and have the individual amino acid residue sequences as follows:

| Designation | (SEQ ID NO) | Amino Acid Residue Sequence |
| --- | --- | --- |
| Fe-1 | 42 | SASMRSAIGLWRTMDY |
| Fe-2 | 43 | GDREIFHMQWPLRVDV |
| Fe-3 | 44 | SQNPQQVCGVRCGQDK |
| Fe-4 | 45 | GNRLSSGHLLKQGQDG |
| Fe-5 | 46 | GGSDWQIGACCREDDL |
| Fe-6 | 47 | GMVSMMGQSRPTQCDC |
| Fe-7 | 48 | GVIKWIRRWVRTARDV |
| Fe-8 | 49 | GWFWRLLPTPRAPSDV |

As described above for Cu-reactive antibodies, those reactive antibodies selected for binding to Zn(II), Pb(II), Ce(III), and Fe(III) exhibit unique sequence characteristics. Zn(II)-selected sequences show the His rich character seen for Cu(II) and one sequence which is identical to that selected with Cu(II). Only one clone is rich in carboxylates. Selection for His, Cys, Asp, and Glu is expected based on studies of natural proteins as described by Vallee et al., Biochem., 29:5647–5659 (1990). The coordinating ligands from sequences selected for binding to Pb(II), Ce(III), and Fe(III) are less obvious. A number of features are apparent. Pb(II) sequences are rich in Asp and Glu (10% of randomized residues). For comparison, Ce(III), Fe(III), and Cu(II) selected sequences contained these residues at 7, 4, and 5% respectively. The oxygen-containing ligands Ser, Thr, and Tyr constitute 18% of Pb(II) and Ce(III) sequences as compared to 11 and 9% for Fe(III) and Cu(II). The Ser and Thr amino acid residues are over-represented at the synthesis level and are present at 3 and 2 parts per 32. Fe(III)-reactive sequences are enriched to the 10% level for the sulfur containing residues Cys and Met.

Thus, for all the metal binding antibodies of this invention described above, within the pool of 20 commonly occurring amino acids, almost half have been observed to participate in metal ligation within proteins (Asp, Cys, Glu, His, Met, Ser, Thr, Tyr, and Trp). Main chain carbonyl oxygens and amide nitrogens can also be utilized to coordinate metals. Most protein engineering efforts utilize design strategies based on analogy as described by Tainer et al., Curr. Opin. Biotech., 2:582–591 (1991). While such a strategy may be sufficient for the transfer of known metal binding motifs into alternative proteins, it limits the ability to explore and exploit novel reactivities for most of the periodic table.

The ability to selectively sort proteins in vitro for metal ligation using the methods of this invention provides the distinct advantage of overcoming the limitations in scope resulting from natural phylogenies. Furthermore, the randomization and selection methods used in obtaining the metal-binding antibodies of the instant invention generate a variety of ligating groups which provide a multiplicity of coordination numbers and geometries resulting in the alteration of the reactivity of the bound metal.

A further embodiment of this invention are antibodies containing metal binding sites selected against compounds containing the elements listed in the Periodic Table of the Elements under columns 3–14 as described in Chemical and Engineering News, 63:27 (1985) and as described in Section C5 below.

1. General Uses for Metal Binding Site-Containing Polypeptides and Methods of Preparation The present inventions provide a variety of utilities, as discussed further herein. In particular, a metal binding site polypeptide, and more particularly a monoclonal antibody of this invention, provides a unique reagent having both therapeutic and diagnostic utilities.

Insofar as a polypeptide or antibody of this invention binds to a preselected metal ion-containing molecule, it may be used as a reagent to bind to the metal ion as a metal ion chelator. In this way the reagent is useful for the isolation of metal ions and metal ion-containing molecules, as in purification procedures where the presence of metal ion is undesirable.

Alternatively, the presence of a metal ion binding site may be used as a means for detection the presence of the polypeptide by detecting the presence of a metal ion associated with the polypeptide to which it is bound. Exemplary methods include magnetic resonance imaging, metal isotope labelling and other detection methods sensitive for a metal ion-containing molecule.

The magnetic antibodies described herein are particularly useful in magnetic imaging and magnetic separation schemes.

In another embodiment, the invention describes the iterative method for producing useful metal binding polypeptides, particularly catalytic antibodies which use the metal ion as a cofactor in catalysis.

C. Methods for Producing Metal Binding Sites

The present invention relates generally to methods for producing polypeptide-defined binding sites. The method involves the preparation of libraries of different binding sites on a phage display protein using degenerate oligonucleotides and primer extension reactions to incorporate the degeneracies into the binding site region of the display protein. Thereafter, the display protein is screened for the ability to bind to a metal ion.

1. Phagemid Display Proteins

The display of the metal binding sites of this invention on a phagemid can be accomplished on any of the surface proteins of the filamentous phage particle, although particularly preferred are display proteins comprising gene III or gene VIII protein, as described herein. The use of gene III or gene VIII protein as a display protein on filamentous phage has been extensively described elsewhere herein.

Particularly preferred display proteins are fusions involving the use of the phage particle membrane anchor derived from gene III or gene VIII fused to an immunoglobulin heavy or light chain as described herein. In this embodiment, the binding site is displayed in a CDR of the immunoglobulin heavy or light chain, which in turn is a fusion to the membrane anchor domain of the phage's gene III or gene VIII protein.

When using an immunoglobulin heavy or light chain as the display protein, it is preferred to position the binding site within one or more of the complementarity determining regions, CDR1, CDR2 or CDR3. Using the Kabat immunoglobulin amino acid residue sequence position numbering system, the light chain CDR's are as follows: CDR1 (residues 23-35), CDR2 (residues 49-57), and CDR3 (residues 88-98); and the heavy chain CDR's are as follows: CDR1 (residues 30-36), CDR2 (residues 49-66), and CDR3 (residues 94-103). See, Kabat et al., "Sequences of Proteins of Immunological Interest", 5th ed., NIH, (1991).

When mutagenizing a CDR of an immunoglobulin fusion display protein, some, most or all of the CDR can be removed and substituted by the newly incorporated sequences that create the metal binding site. CDRs are very accommodating to variably sized inserts without disrupting the ability of the immunoglobulin to assemble and display the newly randomized and selected amino acid residue sequence.

In one embodiment, a phage display protein can be engineered to contain multiple binding sites. For example, using the heavy chain immunoglobulin as exemplary, binding sites can be created separately by the methods of this invention into one or more of the CDRs, designated CDR1, CDR2 and CDR3. Additionally, one can introduce binding sites into a heavy chain CDR and a light chain CDR, into multiple heavy and light chain CDRs, and the like combinations.

In another embodiment, the phage display protein is engineered to include stabilization features in addition to the stabilization provided by the native structure of the display protein. To that end, cysteine residues can be coded for by the oligonucleotide, such that disulfide bridges can be formed. The placement of the cysteine residues can be varied, such that a loop structure of from about 5 to 20 amino acid residues is formed.

2. Oligonucleotides

The preparation of a metal binding site according to the present invention involves the use of synthetic oligonucleotides designed to introduce a putative binding site into a display protein. Furthermore, the oligonucleotide strategy described herein has particular advantages in creating in a single reaction an extremely large population of different randomized binding sites by the use of degenerate oligonucleotides.

The present invention describes methods for producing binding sites that bind metal ions. The methods generally follow the methods described herein with a few exceptions.

The mutagenizing oligonucleotide has a structure that is generally degenerate throughout the central portion as described in co-pending application Ser. No. 07/826,623 filed Jan. 27, 1992, having the title "Heterodimeric Receptor Libraries Using Phagemids", the teachings of which are hereby incorporated by reference.

The mutagenizing oligonucleotide randomizes the amino acid residue sequence of the immunoglobulin CDR, and the subsequent screening of the expressed phagemid display protein for metal ion binding is conducted as described herein and further in the Examples.

Several oligonucleotide designs were utilized to form a metal binding site of varying lengths comprising a CDR. In one design, a series of 5, 10 or 16 consecutive amino acid residues were randomized by a degenerate oligonucleotide. In another design, select amino acid residues were maintained while the remainder of residues in the site were randomized. Thus, one oligonucleotide introduced a 5 amino acid residue sequence in which the fourth amino acid residue was kept constant as aspartic acid (D). Another oligonucleotide design introduced a 10 amino acid residue sequence in which the first and ninth amino acid residues were kept constant as glycine (G) and aspartic acid (D), respectively. A third oligonucleotide design introduced a 16 amino acid residue sequence in which the first and fifteenth amino acid residues were kept constant as glycine (G) and aspartic acid (D), respectively.

The general structure of an oligonucleotide for use in the present methods has the general formula ANB, where A and B define regions of homology to regions of the display protein gene which flank the site in which a binding site is to be inserted and N defines region of degeneracy in which variable amino acid residues are introduced.

The number of nucleotides for each region (A, B, or N) can vary widely, but must be in triplets so as to preserve the reading frame of the display protein. Typically, A and B are of sufficient length to confer hybridization specificity with the template during the primer extension reaction. Thus, A and B are typically each at least 6 nucleotides, and preferably each at least 9 nucleotides in length, although they can be 12, 15, 18, 21 and up to about 24 nucleotides in length. The N's are typically of a widely variable length coding typically from 3 to 50 amino acid residues, preferably 3 to 24 amino acid residues in length.

Where the display protein is an immunoglobulin, the homologies are directed to the immunoglobulin framework regions (FR) that flank the CDR into which the binding site is to be inserted.

Thus, in one embodiment, the invention contemplates an oligonucleotide useful as a primer for producing a metal binding site in a polypeptide coded for by a hybrid immunoglobulin heavy or light chain gene. The oligonucleotide has 5' and 3' termini and comprises:

i) a nucleotide sequence of about 5 to 50 nucleotides in length at the 3' termini capable of hybridizing to a first framework region of the immunoglobulin gene;

ii) a nucleotide sequence of about 5 to 50 nucleotides in length at the 5' termini capable of hybridizing to a second framework region of the immunoglobulin gene; and iii) a nucleotide sequence between said 5' and 3' termini according to the formula:

$$[NNS]_a$$

where a is a whole integer from 3 to 50, N is independently any nucleotide, S is cytosine (C) or guanosine (G) or analogs thereof, and wherein said 5' and 3' terminal nucleotide sequences have a length of about 6 to 50 nucleotides in length, and sequences complementary thereto.

The choice of framework regions depends on the CDR into which the binding site is to be inserted. Thus, for example, for an insertion into CDR3, the 3' and 5' regions of the oligonucleotides are selected as to be complementary in nucleotide sequence to the coding strand defining FR4 and FR3 that flank CDR3, respectively, where the oligonucleotide is to be complementary to the noncoding (anti-sense) strand of the template DNA.

A preferred and exemplary CDR for insertion of a binding site is the CDR3 of immunoglobulin heavy chain. Particularly preferred is the immunoglobulin heavy chain display protein present in the vectors pC3AP313 and p7EII, described herein.

Oligonucleotides used in the present methods that are particularly preferred for producing a metal binding site of 5 and 10 amino acid residues in the heavy chain of CDR3 have the following respective nucleotide sequence formulas: HCDR5 5'-GTGTATTATTGTGCGAGA(NNS)$_5$ TGGGGCCAAGGGACCACG-3' (SEQ ID NO 50) AND HCDR10 5'-GTGTATTATTGTGCGAGA(NNS)$_{10}$ TGGGGCCAAGGGACCACG-3' (SEQ ID NO 51).

Additionally contemplated for use in this invention is the complementary nucleotide sequence of the preferred oligonucleotide formulation and identified sequences. Specifically, the complementary oligonucleotide has 5' and 3' termini between which is the nucleotide formulation $[SNN]_a$. This alternative embodiment of a complementary oligonucleotide thus hybridizes to the coding (sense) strand of the template DNA.

In another embodiment, the invention contemplates an oligonucleotide useful as a primer for producing a metal binding site in a polypeptide coded for by a hybrid immunoglobulin heavy or light chain gene, where two amino acid residues of the gene are retained. The oligonucleotide has 5' and 3' termini and comprises:

i) a nucleotide sequence of about 5 to 50 nucleotides in length at the 3' termini capable of hybridizing to a first framework region of the immunoglobulin gene;

ii) a nucleotide sequence of about 5 to 50 nucleotides in length at the 5' termini capable of hybridizing to a second framework region of the immunoglobulin gene; and iii) a nucleotide sequence between said 5' and 3' termini according to the formula:

-X-[NNK]$_a$-X-[NNK]-X-, where a is a whole integer from 3 to 50, X is a trinucleotide encoding a native amino acid residue coded by the immunoglobulin gene, N is independently any nucleotide, K is guanosine (G) or thymine (T) or analogs thereof, wherein said internal X is one nucleotide triplet encoding one immunoglobulin gene amino acid residue and wherein said 5' and 3' terminal nucleotide sequences have a length of about 6 to 50 nucleotides in length, and sequences complementary thereto.

A preferred and exemplary CDR for insertion of a binding site is the CDR3 of immunoglobulin heavy chain. Particularly preferred is the immunoglobulin heavy chain display protein present in the vectors pC3AP313 and p7EII, described herein.

Oligonucleotides used in the present methods that are particularly preferred for producing a metal binding site of 10 and 16 amino acid residues in the heavy chain of CDR3 have the first and next to last amino acid residues in the mutagenized CDR kept constant as glycine (G) and aspartic acid (D) residues, respectively. These preferred oligonucleotides have the following respective nucleotide sequence formulas: HCDRD10 5'-GCCGTGTATTACTGTGCGAGA GGT(NNK)<u>7</u> <u>GACNNKT</u>GGGGCCAAGGGACCACGGTC-3' (SEQ ID NO 52) and HCDRD16 5'-GCCGTGTATTACTGTGCGAGA<u>GGT(NNK)<sub>13</sub> GACNNKT</u>GGGGCCAAGGGACCACGGTC-3' (SEQ ID NO 53). The underlined nucleotides in the above oligonucleotide formulations indicate the complete 10 or 16 amino acid residue CDR.

Another preferred oligonucleotide used in the present methods for producing a metal binding site of 5 amino acid residues in the heavy chain of CDR3 has the next to last amino acid residue in the mutagenized CDR kept constant as an aspartic acid (D) residue. This oligonucleotide has the following nucleotide sequence formula: HCDRD5 5'-CGGGTGTATTACTGTGCGAGA<u>(NNK)<sub>3</sub> GACNNKT</u>GGGGCCAAGGGACCACGGTC-3' (SEQ ID NO 54). The underlined nucleotides in the above oligonucleotide formulation indicate the complete 5 amino acid residue CDR.

Additionally contemplated for use in this invention is the complementary nucleotide sequence of the preferred oligonucleotide formulation and identified sequences. Specifically, the complementary oligonucleotide has 5' and 3' termini between which is the nucleotide formulation -X-[MNN]-X-[MNN]$_a$-X-, wherein all elements of the formulation are as presented above. This alternative embodiment of a complementary oligonucleotide thus hybridizes to the coding (sense) strand of the template DNA.

Oligonucleotides for use in the present invention can be synthesized by a variety of chemistries as is well known. An excellent review is "Oligonucleotide Synthesis: A Practical Approach", ed. M.J. Gait, JRL Press, New York, N.Y. (1990). Suitable synthetic methods include, for example, the phosphotriester or phosphodiester methods see Narang et al., Meth. Enzymol., 68:90, (1979); U.S. Pat. No. 4,356,270; and Brown et al., Meth. Enzymol., 68:109, (1979). Purification of synthesized oligonucleotides for use in primer extension and PCR reactions is well known. See, example Ausubel et al., "Current Protocols in Molecular Biology", John Wiley & Sons, New York, (1987). Oligonucleotides for use in the present invention are commercially synthesized by Operon Technologies, Alameda, Calif.

3. Primer Extension Reactions

The term "polynucleotide" as used herein in reference to primers, probes and nucleic acid fragments or segments to be synthesized by primer extension is defined as a molecule comprised of two or more deoxyribonucleotides or ribonucleotides, preferably more than three. Its exact size will depend on many factors, which in turn depends on the ultimate conditions of use.

The term "primer" as used herein refers to a polynucleotide whether purified from a nucleic acid restriction digestion reaction or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarily with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nucl. Acids Res.,* 12:7057–70 (1984); Studier et al., *J. Mol. Biol.,* 189:113–130 (1986); and *Molecular Cloning: A Laboratory Manual, Second Edition,* Sambrook et al., eds., Cold Spring Harbor, N.Y. (1989).

When a primer containing a DNA-dependent RNA polymerase promoter is used the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology,* 6:1197–1202 (1988). RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.,* 89:719–736 (1974).

The choice of a primer's nucleotide sequence depends on factors such as the distance on the nucleic acid from the region of the display protein gene into which a binding site is being introduced, its hybridization site on the nucleic acid relative to any second primer to be used, and the like.

The PCR reaction is performed using any suitable method. Generally it occurs in a buffered aqueous solution, i.e., a PCR buffer, preferably at a pH of 7–9, most preferably about 8. Preferably, a molar excess of the primer is admixed to the buffer containing the template strand. A large molar excess of about $10^4:1$ of primer to template is preferred to improve the efficiency of the process.

The PCR buffer also contains the deoxyribonucleotide triphosphates dATP, dCTP, dGTP, and dTTP and a polymerase, typically thermostable, all in adequate amounts for primer extension (polynucleotide synthesis) reaction. The resulting solution (PCR admixture) is heated to about 90 degrees Celsius (90 C.)–100 C. for about 1 to 10 minutes, preferably from 1 to 4 minutes. After this heating period the solution is allowed to cool to 54 C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40 C. An exemplary PCR buffer comprises the following: 50 mM KCl; 10 mM Tris-HCl; pH 8.3; 1.5 mM MgCl$_2$; 0.001% (wt/vol) gelatin, 200 micromolar (uM) dATP; 200 uM dTTP; 200 uM dCTP; 200 uM dGTP; and 2.5 units *Thermus aquaticus* DNA polymerase I (U.S. Pat. No. 4,889,818) per 100 microliters of buffer. Exemplary PCR amplifications are performed using the buffer system as described in Example 1.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., *The Enzymes,* ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nuc. Acids Res.,* 17:711–722 (1989). Amplification systems based on transcription have been described by Gingeras et al., in *PCR Protocols, A Guide to Methods and Applications,* pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process, as is known for PCR.

PCR is typically carried out by thermocycling i.e., repeatedly increasing and decreasing the temperature of a PCR reaction admixture within a temperature range whose lower limit is about 10 C. to about 40 C. and whose upper limit is about 90 C. to about 100 C. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990); the teachings of which are hereby incorporated by reference.

Preferred PCR reactions using the oligonucleotides and methods of this invention are described in the Examples.

4. Phage Display Vectors

Random mutagenesis of CDRs in a V region and screening methods such as is described by Barbas et al, *Proc. Natl.*

*Acad. Sci., USA*, 89:4457–4461, (1992) can be used for preparing antibodies that contain metal binding specificities.

The methods of the present invention for preparing metal binding sites involve the use of phage display vectors for their particular advantage of providing a means to screen a very large population of expressed display proteins and thereby locate one or more specific clones that code for a desired binding reactivity.

The use of phage display vectors derives from the previously described use of combinatorial libraries of antibody molecules based on phagemids. The combinatorial library production and manipulation methods have been extensively described in the literature, and will not be reviewed in detail herein, except for those feature required to make and use unique embodiments of the present invention. However, the methods generally involve the use of a filamentous phage (phagemid) surface expression vector system for cloning and expressing antibody species of the library.

Various phagemid cloning systems for producing combinatorial libraries have been described by others. See for example the preparation of combinatorial antibody libraries on phagemids as described by Kang et al., *Proc. Natl. Acad. Sci., USA*, 88:4363–4366 (1991); Barbas et al., *Proc. Natl. Acad. Sci., USA*, 88:7978–7982 (1991); Zebedee et al., *Proc. Natl. Acad. Sci., USA*, 89:3175–3179 (1992); Kang et al., *Proc. Natl. Acad. Sci., USA*, 88:11120–11123 (1991); Barbas et al., *Proc. Natl. Acad. Sci., USA*, 89:4457–4461 (1992); and Gram et al., *Proc. Natl. Acad. Sci., USA*, 89:3576–3580 (1992), the disclosures of which are hereby incorporated by reference.

a. Phage Display Vector Structure

A preferred phagemid vector of the present invention is a recombinant DNA (rDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide defining an immunoglobulin heavy or light chain variable region, and (3) a filamentous phage membrane anchor domain. The vector includes DNA expression control sequences for expressing the fusion polypeptide, preferably prokaryotic control sequences.

The filamentous phage membrane anchor is preferably a domain of the cpIII or cpVIII coat protein capable of associating with the matrix of a filamentous phage particle, thereby incorporating the fusion polypeptide onto the phage surface.

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane.

In the phage f1, gene VIII coat protein's membrane spanning region comprises residue Trp-26 through Lys-40, and the cytoplasmic region comprises the carboxy-terminal 11 residues from 41 to 52 (Ohkawa et al., *J. Biol. Chem.*, 256:9951–9958, 1981). An exemplary membrane anchor would consist of residues 26 to 40 of cpVIII. Thus, the amino acid residue sequence of a preferred membrane anchor domain is derived from the M13 filamentous phage gene VIII coat protein (also designated cpVIII or CP 8). Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpIII). Gene III coat protein is present on a mature filamentous phage at one end of the phage particle with typically about 4 to 6 copies of the coat protein.

For detailed descriptions of the structure of filamentous phage particles, their coat proteins and particle assembly, see the reviews by Rached et al., *Microbiol. Rev.*, 50:401–427 (1986); and Model et al., in "The Bacteriophages: Vol. 2", R. Calendar, ed. Plenum Publishing Co., pp. 375–456 (1988).

The secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from *Erwinia carotova* are described in Lei et al., *Nature*, 331:543–546 (1988).

The leader sequence of the pelB protein has previously been used as a secretion signal for fusion proteins (Better et al., *Science*, 240:1041–1043 (1988); Sastry et al., *Proc. Natl. Acad. Sci., USA*, 86:5728–5732 (1989); and Mullinax et al., *Proc. Natl. Acad. Sci., USA*, 87:8095–8099 (1990)). Amino acid residue sequences for other secretion signal polypeptide domains from *E. coli* useful in this invention as described in Oliver, *Escherichia coli* and *Salmonella Typhimurium*, Neidhard, F.C. (ed.), American Society for Microbiology, Washington, D.C., 1:56–69 (1987).

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence. The 3' control sequences define at least one termination (stop) codon in frame with and operatively linked to the heterologous fusion polypeptide.

In preferred embodiments, the vector used in this invention includes a prokaryotic origin of replication or replicon, i.e., a DNA sequence having the ability to direct autonomous replication and maintenance of the recombinant DNA molecule extra chromosomally in a prokaryotic host cell, such as a bacterial host cell, transformed therewith. Such origins of replication are well known in the art. Preferred origins of replication are those that are efficient in the host organism. A preferred host cell is *E. coli*. A preferred strain of *E. coli* is the supE strain as an amber stop codon is translated as glutamine (Q). For use of a vector in *E. coli*, a preferred origin of replication is ColE1 found in pBR322 and a variety of other common plasmids. Also preferred is the p15A origin of replication found on pACYC and its derivatives. The ColE1 and p15A replicon have been extensively utilized in molecular biology, are available on a variety of plasmids and are described at least by Sambrook et al., in "Molecular Cloning: a Laboratory Manual", 2nd edition, Cold Spring Harbor Laboratory Press, New York (1989).

The ColE1 and p15A replicons are particularly preferred for use in one embodiment of the present invention where two "binary" plasmids are utilized because they each have the ability to direct the replication of plasmid in *E. coli* while the other replicon is present in a second plasmid in the same *E. coli* cell. In other words, ColE1 and p15A are non-interfering replicons that allow the maintenance of two plasmids in the same host (see, for example, Sambrook et al., supra, at pages 1.3–1.4). This feature is particularly important when using binary vectors because a single host cell permissive for phage replication must support the independent and simultaneous replication of two separate vectors, for example when a first vector expresses a heavy chain polypeptide and a second vector expresses a light chain polypeptide.

In addition, those embodiments that include a prokaryotic replicon can also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form. The choice of vector to which a transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication (see for example, Rasched et al., *Microbiol. Rev.*, 50:401–427, 1986; and Horiuchi, *J. Mol. Biol.*, 188:215–223, 1986). A preferred filamentous phage origin of replication for use in the present invention is an M13, f1 or fd phage origin of replication (Short et al., *Nucl. Acids Res.*, 16:7583–7600, 1988).

Preferred DNA expression vectors for cloning and expressing a phagemid display protein of this invention are the dicistronic plasmid expression vectors pC3AP313 and p7EII described herein.

It is to be understood that, due to the genetic code and its attendant redundancies, numerous polynucleotide sequences can be designed that encode a contemplated heavy or light chain immunoglobulin variable region amino acid residue sequence. Thus, the invention contemplates such alternate polynucleotide sequences incorporating the features of the redundancy of the genetic code.

Insofar as the expression vector for producing a human monoclonal antibody of this invention is carried in a host cell compatible with expression of the antibody, the invention contemplates a host cell containing a vector or polynucleotide of this invention. A preferred host cell is *E. coli*, as described herein.

The preferred phagemid expression vectors in the form of plasmids that produce a phagemid display protein of this invention were deposited pursuant to Budapest Treaty requirements with the American Type Culture Collection (ATCC), Rockville, Md., for co-pending application Serial No. 08/012,566, filed Feb. 2, 1993, entitled "Methods for Producing Polypeptide Binding Sites", the disclosures of which are hereby incorporated by reference. The phagemid expression vectors, pC3AP313 and p7EII, have the respective ATCC Accession Numbers 75408 and 75409.

b. Use of Phagemid Display Vectors to Produce a Metal Binding Site

A phagemid vector for use herein is a recombinant DNA (rDNA) molecule containing a nucleotide sequence that codes for and is capable of expressing an antibody-derived heterodimeric protein on the surface of the phagemid in the form of a phagemid display protein. Exemplary and preferred phagemid vectors are the plasmids pC3AP313 and p7EII described herein and further in Example 1.

The method for producing a metal binding site in a phagemid display protein generally involves (1) introducing a heavy or light chain V region-coding gene of interest into the phagemid display vector; (2) introducing a metal binding site into the phagemid display protein vector by primer extension with an oligonucleotide containing regions of homology to a CDR of the antibody V region gene and containing regions of degeneracy for producing randomized coding sequences as described herein, to form a large population of display vectors each capable of expressing different putative binding sites displayed on a phagemid surface display protein, (3) expressing the display protein and binding site on the surface of a filamentous phage particle, and (3) isolating the surface-expressed phage particle using affinity techniques such as panning of phage particles against a preselected metal cation, thereby isolating one or more species of phagemid containing a display protein containing a binding site that binds a preselected metal cation.

As a further characterization of the produced metal binding site, the nucleotide and corresponding amino acid residue sequence of the gene coding the randomized CDR is determined by nucleic acid sequencing. The primary amino acid residue sequence information provides essential information regarding the binding site's reactivity.

An exemplary preparation of a metal binding site in the CDR3 of a heavy chain of an immunoglobulin is described in the Examples. The isolation of a particular vector capable of expressing a metal binding site of interest involves the introduction of the dicistronic expression vector able to express the phagemid display protein into a host cell permissive for expression of filamentous phage genes and the assembly of phage particles. Typically, the host is *E. coli*. Thereafter, a helper phage genome is introduced into the host cell containing the phagemid expression vector to provide the genetic complementation necessary to allow phage particles to be assembled.

The resulting host cell is cultured to allow the introduced phage genes and display protein genes to be expressed, and for phage particles to be assembled and shed from the host cell. The shed phage particles are then harvested (collected) from the host cell culture media and screened for desirable metal cation binding properties. Typically, the harvested particles are "panned" for binding with a preselected metal cation. Another preferred method of screening involves the use of metal chelate affinity chromatography as described in the Examples. The strongly binding particles are then collected, and individual species of particles are clonally isolated and further screened for binding to the metal cation. Phage which produce a binding site of desired metal binding specificity are selected.

With the above-described procedure, the resulting phagemids and phagemid display proteins were screened and selected for binding to either $Cu^{2+}$, $Zn^{2+}$, $Pb^{2+}$, $Ce^{3+}$, $Fe^{3+}$, or magnetite, and the metal binding site containing clones were sequenced to determine the binding site sequence. Preferred metal binding site sequences were described earlier herein. The preferred antibody libraries for use in this invention are libraries E and F resulting from mutagenesis of the phagemid expression vector pC3AP313. Libraries E and F, respectively, contained 16 and 10 amino acid residue sequence-containing mutagenized CDR3s. These libraries retain the structurally significant aspartic acid residue in the penultimate position (the next to last position) within the CDR3.

5. Preferred Metals for Selecting Metal Binding Site-Specific Monoclonal Antibodies A randomized (mutagenized) CDR-containing antibody becomes a metalloantibody when it is complexed with a metal cation. Metal cations (cofactor cations) suitable for complexing with a metal binding protein of this invention are any of the transition state metals of the periodic table, and the non-transition state metals calcium (Ca), zinc (Zn), cadmium (Cd), cerium (Ce), mercury (Hg), strontium (Sr), and barium (Ba), which metals have the capacity to occupy a tetrahedral oxidation state and thereby complex with said protein through coordinated ligands provided by the three contact amino acid residues on the metal binding protein. Preferred metal cations for use in a metalloprotein of this invention are divalent and trivalent cations. Preferred divalent cations include Cu(II), Zn(II), Ni(II), Co(II), Fe(II), Ag(II), Mn(II), Pb(II) or Cd(II), and more preferably Cu(II), Zn(II), Ni(II) and Pb(II). Preferred trivalent cations include Ce(III) and Fe(III), the latter in the form of iron oxide or iron chloride.

In preferred embodiments, the metal cation of a catalytic metalloantibody is Cu(II), and a preferred chemical reaction is the non-oxidative hydrolysis reactions as well as oxidative reactions. Other preferred embodiments include the following: 1) Fe(III) results in the oxidative cleavage of proteins and could be utilized as a cofactor to produce antibodies which cleave proteins at defined sequences; 2) Pb(II) and Ni(III) is utilized to cleave nucleic acids; and 3) Lanthanide cerium, specifically, Ce(III) hydroxide clusters, is used to catalyze the hydrolysis of cAMP.

Metalloantibodies are formed by preparing an antibody having a mutagenized CDR resulting in the formation of a metal binding site of the present invention, and then exposing the metal binding protein to a selected metal cation, preferably in a buffered aqueous medium, for a time sufficient to allow a metal-protein coordination complex to form. Preferred are the metalloantibodies prepared and described in the Examples.

D. Methods for Selection of Catalytic Synthetic Antibodies

A preferred embodiment is general iterative strategy using the methods of this invention for selection of catalytic synthetic antibodies as shown in FIG. 2. The first step in this strategy involves selection of sequences within the antibody combining site which coordinate metal. The preferred regions in which mutagenesis is performed are the CDRs. Selection is most easily achieved by immobilization of the target. Preferred for use is the immobilization of a metal ion utilized a support derivatized with a chelating agent. Such iminodiacetic acid supports are suitable for the immobilization of many metals. Furthermore, this chelating agent occupies a limited number of coordination sites on the metal and provides the metal with a number of vacant sites ($H_2O$) which are utilized to select coordinating antibodies from the library. Preferred alternatives to an inert support are synthetic transition-state analogs that immobilize the metal for selection.

The second step of the method for selecting synthetic catalytic antibodies involves the diversification of the library either by chain shuffling or mutagenesis of another CDR. From this pool of antibodies which coordinate metal, a second selection step is then utilized to optimize binding to a hapten which may also provide a site to coordinate metal although coordination to the substrate may not be necessary so long as the metal participates in the chemistry. For example, a Zn atom coordinated to one CDR may be utilized to deliver a hydroxide ion to the carbonyl carbon of a peptide bound to another region of the antibody molecule. The light chain CDR3 may be the most desirable region to install metal binding as the extended heavy chain CDR3 could be utilized to provide the hapten binding pocket, similar to that seen with known copper containing proteins that coordinate copper within a loop of a Greek key folded domain as described by Adam, *Adv. Prot. Chem.*, 42:145–197 (1991). Antibodies exhibit this same fold. To that end, a naturally occurring copper-binding antibody derived from a myeloma patient has been previously described by Baker et al., *J. Biol. Chem.*, 253:8444–8451 (1978). A mercury-binding antibody has also recently been described by Wylie et al., *Proc. Natl. Acad. Sci., USA*, 82:4104–4108 (1992).

Preferred metal binding sites in the antibody combining site useful in catalysis include the following: 1) Cu(II) has been utilized to catalyze nonoxidative hydrolysis reactions as well as oxidative reactions as described by Chiou, *J. Biochem.*, 94:1259–1267 (1983) and Fife et al., *J. Am. Chem. Soc.*, 105:1638–1642 (1983); 2) Fe(III) is particularly interesting for the oxidative cleavage of proteins and could be utilized as a cofactor to produce antibodies which cleave proteins at defined sequences as described by Rana et al., *J. Am. Chem. Soc.*, 112:2457–2458 (1990); 3) Pb(II) and Ni(III) have been utilized to cleave RNA and DNA, respectively, as described by Brown et al., *Nature*, 303:543–546 (1983) and Cheng et al., *Angew. Chem. Int. Ed. Engl.*, 32:277–278 (1993); and 4) Cerium(III) hydroxide clusters have recently been demonstrated to catalyze the hydrolysis of cAMP with a $10^{11}$ fold rate enhancement as described by Sumacka et al., *J. Chem. Soc., Chem. Commun.*, 1707–1708 (1992). Cerium, thus, is a particularly interesting metal to incorporate into antibodies in an effort to produce artificial restriction enzymes. Furthermore, cerium serves as an example of a catalytically interesting metal for which there is no known naturally occurring protein from which to design a metal binding site.

E. Metal Binding Site Compositions and Uses Thereof

1. Metal Binding Site Monoclonal Antibodies

The present invention describes, in one embodiment, human monoclonal antibodies that contain a binding site as described herein and that bind specifically to a preselected target molecule. The invention also describes cell lines that produce the antibodies, methods for producing the cell lines, and methods for producing the human monoclonal antibodies.

Insofar as a display protein of this invention on a phagemid particle is, in preferred embodiments, a fusion protein between an immunoglobulin heavy or light chain and a filamentous phage membrane anchor, it is to be understood that the display protein is, in effect, an engineered immunoglobulin heavy or light chain into which a binding site has been introduced by the methods of this invention. Furthermore, in many embodiments, the expression of the display protein is prepared on the phagemid surface as a heterodimer formed between immunoglobulin heavy and light chain polypeptides, with one or the other being a fusion protein with the membrane anchor. Thus, where the heavy chain is used as the fusion protein, a display protein in preferred embodiments comprises a Fab fragment having an anchored heavy chain associated with a light chain.

The preparation of cell lines producing monoclonal antibodies of the invention is described in great detail further herein, and can be accomplished using the phagemid vector mutagenesis methods described herein, and using routine screening techniques which permit determination of the elementary binding patterns of the monoclonal antibody of interest indicative that the binding site has been produced. Thus, if a human monoclonal antibody being tested binds to the preselected target molecule, then the human monoclonal antibody being tested and the human monoclonal antibody produced by the phagemid in a host cell of the invention are considered equivalent.

It is also possible to determine, without undue experimentation, if a human monoclonal antibody has the same (i.e., equivalent) specificity as a human monoclonal antibody of this invention by ascertaining whether the former prevents the latter from binding to a preselected target molecule. If the human monoclonal antibody being tested competes with the human monoclonal antibody of the invention, as shown by a decrease in binding by the human monoclonal antibody of the invention in standard competition assays for binding to the target molecule when present in the solid phase, then it is determined that the two monoclonal antibodies bind to the same, or a closely related, epitope.

Still another way to determine whether a human monoclonal antibody has the specificity of a human monoclonal antibody of the invention is to pre-incubate the human monoclonal antibody of the invention with the target molecule with which it is normally reactive, and then add the human monoclonal antibody being tested to determine if the human monoclonal antibody being tested is inhibited in its ability to bind the target molecule. If the human monoclonal antibody being tested is inhibited then, in all likelihood, it has the same, or functionally equivalent, epitopic specificity as the monoclonal antibody of the invention.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence.

Particularly preferred are human monoclonal antibodies having the binding specificity of the monoclonal antibodies produced in $E.\ coli$ microorganisms or produced by plasmid vectors that are deposited with the ATCC, as described further herein.

Use of the term "having the binding specificity of" indicates that equivalent monoclonal antibodies exhibit the same or similar immunoreaction (binding) properties and compete for binding to a preselected target molecule.

The term "conservative variation or substitution" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

The term "conservative variation" also includes the use of a substituted amino acid in place of an unsubstituted parent amino acid provided that antibodies having the substituted polypeptide also bind to the preselected target molecule. Analogously, another preferred embodiment of the invention relates to polynucleotides which encode the above noted heavy and/or light chain polypeptides and to polynucleotide sequences which are complementary to these polynucleotide sequences. Complementary polynucleotide sequences include those sequences which hybridize to the polynucleotide sequences of the invention under stringent hybridization conditions.

Human monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies.

The invention contemplates, in one embodiment, a monoclonal antibody expressed on the surface of bacteriophage as a phagemid display protein of this invention produced by the present methods.

In another preferred embodiment, the invention contemplates a truncated immunoglobulin molecule comprising a Fab fragment derived from a human monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods. A preferred method of producing a soluble Fab fragment is described herein.

In one embodiment, the invention describes a class of human monoclonal antibodies which immunoreact with metal cations including Cu(II), Zn(II), Ni(II), Pb(II), Ce(III), Fe(III), iron oxide and the like. The antibodies were produced by the present methods in which a metal binding sites in a CDR3 of an immunoglobulin heavy chain variable domain were obtained as a result of the mutagenesis of the CDR3 followed by selection on metals, as described in the Examples.

The resulting population of display vectors containing a metal binding site in the display protein were screened first for binding activity by metal chelate affinity chromatography or by panning against the target metal as described in the Examples. Thereafter, selected members of the population of display vectors with metal binding activity were isolated, soluble Fab expression was engineered into each of the selected vectors as described in the Examples, and the resulting soluble Fab were expressed, and screened for binding or other functional activities.

The binding properties of the soluble purified Fabs were then analyzed by ELISA against metal ions immobilized by means of a support derivatives with a chelating agent, such as EDTA. A preferred support for use in this invention is iminodiacetic acid (IDA) complexed with bovine serum albumin (BSA) and the preselected metal. The chelating agent functions by occupying a limited number of coordination sites on the metal and provides the metal with a number of vacant sites that are utilized to select coordinating antibodies from a phagemid library. A preferred alternative to an inert support is the use of synthetic transition-state analogs, the design of which is familiar to one of ordinary skill in the art, that are used to immobilize the metal for selection.

Anti-metal human monoclonal antibodies were identified which have the desirable property of high affinity binding to selected metals with diversity within a class of metal binders. For example, three of the copper-reactive antibodies exhibited unique binding characteristics, as described in the Examples. Data presented in the Examples illustrates anti-metal human monoclonal antibodies produced by the methods of this invention that are potent metal binders as compared to those anti-metal antibodies produced by conventional means.

Particularly preferred human monoclonal anti-metal antibodies are those having the immunoreaction (binding) specificity of a monoclonal antibody having heavy and light chain immunoglobulin variable region amino acid residue sequences in pairs (H:L) where the light chain is the light chain encoded by the plasmid vector pC3AP313 described herein, and referred to as light chain 313, or L313, and the heavy chain has one of the recited binding sites, and conservative substitutions thereof. The designation of a human monoclonal antibody with a colon, e.g., H:L313 is to connote a H:L pair formed by the heavy and light chain, respectively, in which the light chain is the preferred L313 light chain described herein.

2. Catalytic Monoclonal Antibodies with Metal Binding Sites

A particularly preferred embodiment involves using the anti-metal antibodies of the present invention to produce catalytic antibodies, i.e., antibodies having a metal binding site which can participate in promoting catalysis. Thus, the invention contemplates producing a metalloantibody which has the capacity of promoting a predetermined chemical reaction, i.e., a catalytic metalloantibody. Catalytic antibodies have been described by Tramontano et al., Science, 234:1566–1570 (1986); Pollack et al., Science, 234:1570–1573 (1986); Janda et al., Science, 241:1188–1191 (1988); Janda et al., Science, 244:437–440 (1989), and in U.S. Pat. No. 4,659,567, No. 4,900,674, No. 5,030,717, No. 5,079,152 and No. 5,126,258, the disclosures of which are hereby incorporated by reference. In this embodiment, a preselected antigen with which the antibody combining site immunoreacts is also a substrate for a reaction that is promoted by the metalloantibody.

3. Metal Chelation by Monoclonal Antibodies Containing Metal Binding Sites

A metal binding protein can function as a metal ion chelator. Thus, the metal binding antibodies of this invention are suitable for use as metal ion chelators. One of the well-characterized biological chelator of metals is metallothionein which is a ubiquitous, low-molecular weight, metal-binding protein that participates in metal metabolism and detoxification as described by Morelock et al., in "Metallothionein II", Experientia Supplementum (Birkhaeuser, Basel), 52:247–253 (1987). Metallothionein has been shown to bind metals, such as technetium or indium, useful for targeted radiodiagnosis or therapy.

Generally, for use in radioimmunoimaging, chelators are chemically conjugated to antibodies. The disadvantage of the conjugation approach is that the process may result in decreased immunoreactivity of the conjugated antibody or lead to increased protein aggregation. To overcome these deleterious effects, chimeric antibodies have been produced in which the metallothionein chelator has been engineered into the context of an immunoreactive antibody by means of recombinant DNA techniques as described by Das et al., Proc. Natl. Acad. Sci., USA, 89:9749–9753 (1992) and Sawyer et al., Proc. Natl. Acad. Sci., USA, 89:9754–9758 (1992), the disclosures of which are hereby incorporated by reference. The resultant chimeric antibody was shown to efficiently target to the specific antigen while allowing for detection of the metallothionein-chelated radioimaging material.

The metal-binding antibodies of this invention provide further advantages in that instead of creating chimeric antibodies, any number of chelating antibodies with unique specificities and binding characteristics can be selected by screening against specific target molecules, such as radioimaging reagents. Another embodiment of this invention is the preparation of such metal-chelating antibodies that exhibit immunoreactivity against a preselected antigen, such as a hapten or protein, as described herein for the selection of catalytic antibodies and as shown in FIG. 2.

F. Therapeutic and Diagnostic Compositions

The present invention contemplates therapeutic and diagnostic compositions useful for practicing the therapeutic or diagnostic methods described herein. Therapeutic compositions of the present invention contain a physiologically tolerable carrier together with at least one species of human monoclonal antibody as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. Thus, an antibody molecule-containing composition can take the form of solutions, suspensions, tablets, capsules, sustained release formulations or powders, or other compositional forms.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A composition contains a human monoclonal antibody of the present invention, typically in an amount of at least 0.1 weight percent of antibody per weight of total composition. A weight percent is a ratio by weight of antibody to total composition. Thus, for example, 0.1 weight percent is 0.1 grams of antibody per 100 grams of total composition.

Preferably, an antibody-containing composition typically contains about 10 micrograms (ug) per milliliter (ml) to about 100 milligrams (mg) per ml of antibody as active ingredient per volume of composition, and more preferably contains about 1 mg/ml to about 10 mg/ml (i.e., about 0.1 to 1 weight percent).

G. Therapeutic Methods

In view of the benefit of using human monoclonal antibodies in vivo in human patients, the presently described antibodies are particularly well suited for in vivo use as a therapeutic reagent for blocking or inhibiting the function of the target molecule which the antibody binds or for catalyzing therapeutically relevant reaction involving a target molecule. The method comprises contacting a sample believed to contain the target molecule with a composition comprising an effective amount of a human monoclonal antibody of this invention which binds the target molecule.

For in vivo modalities, the method comprises administering to the patient an effective amount of a physiologically tolerable composition containing a human monoclonal antibody of the invention.

The dosage ranges for the administration of the monoclonal antibodies of the invention are those large enough to produce the desired effect. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

An effective amount of an antibody of this invention is typically an amount of antibody such that when administered in a physiologically tolerable composition is sufficient to achieve a plasma concentration of from about 0.1 ug/ml to about 100 ug/ml, preferably from about 1 ug/ml to about 5 ug/ml, and usually about 5 ug/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The human monoclonal antibodies of the invention can be administered parenterally by injection or by gradual infusion over time. Although the target molecule can typically be accessed in the body by systemic administration and therefore most often treated by intravenous administration of compositions, other tissues and delivery means are contemplated where there is a likelihood that the tissue targeted contains the target molecule. Thus, human monoclonal antibodies of the invention can be administered intravenously, intraperitoneally, intramuscularly, subcutaneously, intracavity, transdermally, and can be delivered by peristaltic means.

The compositions containing a human monoclonal antibody of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired effect in association with the required diluent; i.e., carrier, or vehicle.

The compositions are administered in a manner compatible with the dosage formulation, and in a effective amount. The quantity to be administered depends on the subject to be treated, capacity of the subject's system to utilize the active ingredient, and degree of effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or administration. Alternatively, continuous intravenous infusion sufficient to maintain concentrations in the blood in the ranges specified for in vivo therapies or methods are contemplated.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of Synthetic Metal Binding Sites Within the Heavy Chain CDR3 Domain of a Phagemid Fab Display Protein Produced by a Dicistronic Expression Vector The binding sites of this invention as described herein were incorporated into a complementary determining region (CDR) in the antibody heavy chain of a selected phagemid expression vector. The term "binding site" as defined herein is any region of a protein or polypeptide that participates in protein—target molecule interactions. The CDR3 encoding a heavy chain Fab was randomized by PCR mutagenesis followed by overlap polymerase chain reaction (PCR) amplification to create nucleotide sequences that encode amino acid residue sequences that bind selected metals oxides or metal salts, specifically, magnetite ($Fe_3O_4$), copper, zinc, lead, cerium and iron. These residues were randomly amplified into the CDR3 of the heavy chain as described below in either the surface Fab display phagemid expression vectors, pC3AP313 or p7EII. Selection for binding to metals was then performed as described in Example 3.

Both of the phagemid expression vectors, pC3AP313 and p7EII, used in this invention were deposited for co-pending application, Ser. No. 08/012,566 filed Feb. 2, 1993, entitled "Methods for Producing Polypeptide Binding Sites". The deposited expression vectors, pC3AP313 and p7EIII, have been assigned the ATCC accession numbers 75408 and 75409. The p7EII expression vector (also referred to as pC3-TT7E), containing the sequences for encoding a human anti-tetanus toxin antibody where the heavy chain was fused to the coat protein encoded by bacteriophage gene 3, has been described by Barbas et al., *Proc. Natl. Acad. Sci., USA*, 88:7978–7982 (1991), the disclosure of which is hereby incorporated by reference. The vector contains the expression elements present in pC3AP313 as described in Example 2. The resultant metal binding site-encoding PCR products amplified from either pC3AP313 or P7EII were purified, digested and ligated into pC3AP313 for expression as described in Example 2.

For preparing PCR products that encode binding sites that exhibited specificity for metals, two separate PCR reactions were performed followed by overlap PCR. In the first PCR amplification reaction, the 5' end of the heavy chain beginning at framework 1 and extending to the 3' end of framework 3 was amplified. In the second PCR amplification reaction, the CDR3 was mutagenized to produce sequences that encode metal binding sites. The amino acid residue position of the heavy chain CDR3 corresponded to Kabat numbers 94–103. This was accomplished through the use of a pool of oligonucleotide primers synthesized with a degenerate region sandwiched between and contiguous with conserved framework 3 and 4 region sequences. Degenerate oligonucleotide primers were designed for encoding amino acid residue sequences of 5, 10 or 16 amino acid residues in length comprising the resultant CDR3.

The amplification products resulting from the second PCR, each having a randomized CDR3 consisting of various preselected lengths as described below, began at the 3' end of framework 3 and extended to the 3' end of the CH1 region. The pool of degenerate oligonucleotide primers were designed to result in the amplification of products having a 5' end that was complementary to and overlapped with the 3' end of the products of the first PCR reaction product. Thereafter, the two separate PCR reaction products were pooled and subjected to a third PCR reaction in which the overlapping region between the two products was extended to result in a complete heavy chain from framework 1 through framework 4 having a randomized CDR3.

A. PCR Amplifications With p7EII as Template

For amplifications where the p7EII surface display expression vector was selected for the PCR template, the first PCR reaction resulted in the amplification of the region of the heavy chain fragment in the p7EII phagemid beginning at framework region 1 and extending to the end of framework region 3 which was located 5' to CDR3, resulting in a total length of approximately 400 base pairs in length.

To amplify this region, the following primer pairs were used. The 5' coding oligonucleotide primer, FTX3, having the nucleotide sequence 5'-GCAATTAACCCTCACTAAAGGG-3' (SEQ ID NO 55), hybridized to the noncoding strand of the heavy chain corresponding to the region 5' of and including the beginning of framework 1. The 3' noncoding oligonucleotide primer, B7EFR3, having the nucleotide sequence 5'-TCTCGCACAATAATACACGGC-3' (SEQ ID NO 56), hybridized to the coding strand of the heavy chain corresponding to the 3' end of the framework 3 region. The oligonucleotide primers were synthesized by Operon Technologies, Alameda, Calif.

The PCR reaction was performed in an 100 microliter (ul) reaction containing 1 microgram (ug) of each of oligonucleotide primers FTX3 and B7EFR3, 8 ul 2.5 millimolar (mM) dNTP's (dATP, dCTP, dGTP, dTTP), 1 ul Taq polymerase (Perkin-Elmer Corp., Norwalk, CT), 10 nanogram (ng) of template p7EII, and 10 ul of 10X PCR buffer purchased commercially (Perkin-Elmer Corp.). Thirty-five rounds of PCR amplification in a Perkin-Elmer Cetus 9600 GeneAmp PCR System thermocycler were then performed. The amplification cycle consisted of denaturing at 94 degrees C. (94 C.) for one minute, annealing at 47 C. for one minute, followed by extension at 72 C. for two minutes. To obtain sufficient quantities of amplification product, 15 identical PCR reactions were performed and the products were then pooled.

The resultant PCR amplification products containing the sequence for encoding an RGD peptide were then gel purified on a 1.5% agarose gel using standard electroelution techniques as described in "Molecular Cloning: A Laboratory Manual", Sambrook et al., .eds., Cold Spring Harbor, N.Y. (1989). Briefly, after gel electrophoresis of the digested PCR amplified Fab-display encoding synthetic binding sites, the region of the gel containing the DNA fragments of predetermined size were excised, electroeluted into a dialysis membrane, ethanol precipitated and resuspended in buffer containing 10 mM Tris-HCl [Tris(hydroxymethyl) aminomethanehydrochloride]at pH 7.5 and 1 mM EDTA (ethylenediaminetetraacetic acid) to a final concentration of 50 ng/milliliter (ng/ml).

The resultant purified PCR amplification products were then used in an overlap extension PCR reaction with the products of the second PCR reaction, both as described below, to recombine the two products into reconstructed heavy chains containing mutagenized CDR3s.

The second PCR reaction resulted in the amplification of the heavy chain from the 3' end of framework region 3 extending to the end of CH1 region which was approximately 390 base pairs (bp) in length. To amplify this region for encoding 5 random amino acid residues comprising the CDR3, the following primer pairs were used. The 5' coding oligonucleotide primer pool, designated HCDR5, had the nucleotide sequence represented by the formula, 5'-GTGTATTATTGTGCGAGANNSNNSNNSNNSNNST-GGGGCCAAGGGACCACG-3' (SEQ ID NO 50), where N is A, C, G, or T and S is either C or G. The 5' end of the primer pool is complementary to the 3' end of framework 3 represented by the complementary nucleotide sequence of the oligonucleotide primer B73FR3 and the 3' end of the primer pool is complementary to the 5' end of framework 4. The region between the two specified ends of the primer pool is represented by a 15-met degeneracy of 5 NNS triplets that ultimately encodes a diverse population of mutagenized CDR3s of 5 amino acid residues in length. The 3' noncoding oligonucleotide primer, CG1z, as described by Persson et al.,

*Proc. Natl. Acad. Sci., USA,* 88:2432–2436 (1991), having the nucleotide sequence 5'-GCATGTACTAGTTTTGTCACAAGATTTGGG-3' (SEQ ID NO 57), hybridized to the coding strand of the heavy chain corresponding to the 3' end of CH1. The second PCR reaction was performed on the p7EII in a 100 ul reaction as described above containing 1 ug of each of oligonucleotide primers HCDR5 and CG1z. The resultant PCR amplification products were then gel purified as described above.

One hundred nanograms of gel purified products from the first and second PCR reactions were then admixed with 1 ug each of FTX3 and CG1z oligonucleotide primers as a primer pair in a final PCR reaction to form a complete heavy chain fragment by overlap extension. The PCR reaction admixture also contained 10 ul 10X PCR buffer, 1 ul Taq polymerase and 8 ul 2.5 mM dNTP's as described above. The PCR reaction was performed as previously described. To obtain sufficient quantities of amplification product, 15 identical PCR reactions were performed as described above. The resulting heavy chain fragments, beginning at framework 1 and extending to the end of CH1 and having a randomly mutagenized CDR3 for encoding 5 amino acid residues, were approximately 790 base pairs in length. The heavy chain fragment amplification products from the 15 reactions were first pooled and then gel purified as described above prior to their incorporation into the pC3AP313 surface display phagemid expression vector to form a library as described in Example 2. The resulting phagemid library was designated 7-5.

In addition to randomizing the CDR3 in p7EII for expressing 5 amino acid residues, PCR amplifications were performed for expressing a CDR3 containing 10 amino acid residues. Two separate PCR amplifications were performed as described above with the only exception being that, in the second reaction, the 5' coding degenerate primer, designated HCDR10, used to encode 10 random amino acid residues in the CDR3 had the formula: 5'-GTGTATTATTGTGCGAGANNSNNSNNSNNSNNSN-NSNNSNNSNNSNNSTGGGGCCAAGGGACCACG-3' (SEQ ID NO 51), where N is A, C, G or T and S is C or G. The resultant products were pooled and purified as described above prior to insertion into pC3AP313 surface display phagemid expression vector to form a library as described in Example 2. The resulting phagemid library was designated 7-10.

B. PCR Amplifications With pC3AP313 as Template

For amplifications where the pC3AP313 surface display expression vector was selected for the PCR template, the first PCR reaction resulted in the amplification of the region of the heavy chain fragment in the pC3AP313 phagemid beginning at framework region 1 and extending to the end of framework region 3 which was located 5' to CDR3, resulting in a total length of approximately 400 base pairs in length. The degenerate primer designed for use with the pC3AP313 template resulted in the retention of a conserved aspartic acid residue in the next to last position in the CDR3. The retention of the aspartic acid residue in this position is preferred for use in this invention as the expressed proteins containing this residue exhibit high affinity binding characteristics as described in Example 3.

To amplify the 5' end of the heavy chain from framework 1 to the end of framework 3, the following primer pairs were used. The 5' coding oligonucleotide primer, FTX3, having the nucleotide sequence 5'-GCAATTAACCCTCACTAAAGGG-3' (SEQ ID NO 55), hybridized to the noncoding strand of the heavy chain corresponding to the region 5' of and including the beginning of framework 1. The 3' noncoding oligonucleotide primer, BFR3U, having the nucleotide sequence 5'-TCTCGCACAGTAATACACGGCCGT-3' (SEQ ID NO 58), hybridized to the coding strand of the heavy chain corresponding to the 3' end of the framework 3 region. The oligonucleotide primers were synthesized by Operon Technologies.

The PCR reaction was performed in an 100 ul reaction as described above with the exception that 10 ng of template pC3AP313 were used. The resultant PCR amplification products were then gel purified as described above and used in an overlap extension PCR reaction with the products of the second PCR reaction, both as described below, to recombine the two products into reconstructed heavy chains containing mutagenized CDR3s.

The second PCR reaction resulted in the amplification of the heavy chain from the 3' end of framework region 3 extending to the end of CH1 region which was approximately 390 base pairs in length. To amplify this region for encoding a 5 random amino acid residue sequence having the formula NH2-XXXDX-COOH (SEQ ID NO 59), where X is Xaa, any amino acid and D is aspartic acid, in the CDR3, the following primer pairs were used. The 5' coding oligonucleotide primer pool, designated HCDRD5, had the nucleotide sequence represented by the formula, 5'-GCCGTGTATTACTGTGCGAGANNKNNNKNNKGA-CNNKTGGGGCCAAGGGACCACGGTC-3' (SEQ ID NO 54), where N can be A, C, G, or T and K is either G or T. The 5' end of the primer pool is complementary to the 3' end of framework 3 represented by the complementary nucleotide sequence of the oligonucleotide primer BFR3U and the 3' end of the primer pool is complementary to the 5' end of framework 4. The region between the two specified ends of the primer pool is represented by a 12-mer degeneracy of 4 NNK triplets plus a sequence encoding a conserved aspartic acid residue one position from the end of the CDR3. The 3' noncoding oligonucleotide primer, R3B, having the nucleotide sequence 5'-TTGATATTCACAAACGAATGG-3' (SEQ ID NO 60), hybridized to the coding strand of the heavy chain corresponding to the 3' end of CH1.

The sequence NNK represents the coding strand sequence having the complementary sequence NNM in the primer as read from the 3' to 5' direction. Thus, in the primer as listed below the noncoding strand sequence is MNN as read in the 5' to 3' direction. The coding triplet sequence NNK was designed to prevent the production of deleterious stop codons. The only stop codon that could result from the expression of NNK would be an amber mutation that is suppressed when the phagemid is expressed an amber-suppressing host cell, preferably *E. coli* supE strain.

The second PCR reaction was thus performed on the pC3AP313 in an 100 ul reaction as described above containing 1 ug of each of oligonucleotide primers HCDRD5 and R3B. The resultant PCR products encoded a diverse population of mutagenized CDR3s of 5 amino acid residues in length with a conserved aspartic acid residue in the fourth amino acid residue position in the CDR3. The products were then gel purified as described above.

One hundred nanograms of gel purified products from the first and second PCR reactions were then admixed with 1 ug each of FTX3 and R3B oligonucleotide primers as a primer pair in a final PCR reaction to form a complete heavy chain fragment by overlap extension. The PCR reaction admixture also contained 10 ul 10X PCR buffer, 1 ul Taq polymerase and 8 ul 2.5 mM dNTP's as described above. The PCR reaction was performed as previously described.

To obtain sufficient quantities of amplification product, 15 identical PCR reactions were performed. The resulting heavy chain fragments beginning at framework 1 and extending to the end of CH1 and having a randomly mutagenized CDR3 for encoding 5 amino acid residues with a conserved aspartic acid residue were approximately 790 base pairs in length. The heavy chain fragment amplification products from the 15 reactions were first pooled and then gel purified as described above prior to their incorporation into the pC3AP313 surface display phagemid expression vector to form a library as described in Example 2. The resulting phagemid library was designated library G.

In addition to randomizing the CDR3 in pC3AP313 for expressing 5 amino acid residues, PCR amplifications were performed for expressing a CDR3 containing 10 amino acid residues. Two separate PCR amplifications were performed as described above with the only exception being that, in the second reaction, the 5' coding degenerate primer, designated HCDRD10, used to encode 10 amino acid residues comprising the heavy chain CDR3. The degenerate 5' coding primer used here was designed to retain the first amino acid position of a glycine residue in the PC3AP313 template and incorporate a conserved aspartic acid residue in the ninth amino acid position. The HCDRD10 primer had the formula: 5'-GCCGTGTATTACTGTGCGAGAGGTNNK-NNKNNKNNKNNKNNKNNKGACNNKTGGGGCCAA-GGGACCACGGTC-3' (SEQ ID NO 52), where N is A, C, G or T and K is G or T. The amino acid sequences comprising the CDR3 encoded by the use of the HCRD10 primer had the formula NH2-GXXXXXXXXDX-COOH (SEQ ID NO 61), where X is Xaa, any amino acid, G is glycine and D is aspartic acid. The resultant products were pooled and purified as described above prior to insertion into pC3AP313 surface display phagemid expression vector to form a library as described in Example 2. The resulting phagemid library was designated library F.

PCR amplifications using the template pC3AP313 were also performed for expressing a randomized CDR3 containing 16 amino acid residues. The degenerate 5' coding primer used for this amplification was designed to retain the first amino acid position of a glycine residue in the PC3AP313 template and incorporate a conserved aspartic acid residue in the fifteenth amino acid position. Two separate PCR amplifications were performed as described above for the CDR3 having 5 amino acids with the only exception being that, in the second reaction, the 5' coding degenerate primer, designated HCDRD16, used to encode 16 random amino acid residues had the formula: 5'-GCCGTGTATTACTGTGCGAGAGGTNNKNNKNNK-NNKNNKNNKNNKNNKNNKNNKNNKNNKNNKGA-CNNKTGGGGCCAAGGGACCACGGTC-3' (SEQ ID NO 53), where N is A, C, G or T and K is G or T. The amino acid sequences comprising the CDR3 encoded by the use of the HCRD16 primer had the formula NH2-GXXXXXXXXXXXXXXDX-COOH (SEQ ID NO 62), where X is Xaa, any amino acid, G is glycine and D is aspartic acid. The resultant products were pooled and purified as described above prior to insertion into pC3AP313 surface display phagemid expression vector to form a library as described in Example 2. The resulting phagemid library was designated library E.

As described above, the resultant metal binding site encoding PCR products, having heavy chain CDR3s of various lengths amplified from either pC3AP313 or P7EII, were purified, digested and ligated into pC3AP313 for preparation of an expression library as described in Example 2.

2. Production of Phagemid Fab-Displayed Synthetic Binding Sites

In practicing this invention to obtain expression of Fab-display proteins containing a synthetic binding site on a phage surface, the heavy (Fd consisting of $V_H$ and CH1) and light (kappa) chains ($V_L$, $C_L$) of antibodies were first targeted to the periplasm of *E. coli* for the assembly of heterodimeric Fab molecules.

In this system, the first cistron encoded a periplasmic secretion signal (pelB leader) operatively linked to the fusion protein, Fd-cpIII. The second cistron encoded a second pelB leader operatively linked to a kappa light chain. The presence of the pelB leader facilitated the coordinated but separate secretion of both the fusion protein containing the synthetic binding site and light chain from the bacterial cytoplasm into the periplasmic space.

In this process, each chain was delivered to the periplasmic space by the pelB leader sequence, which was subsequently cleaved. The heavy chain containing the synthetic binding was anchored in the membrane by the cpIII membrane anchor domain while the light chain was secreted into the periplasm. Fab molecules were formed from the binding of the heavy chain with the soluble light chains.

A. Preparation of a Dicistronic Expression Vector, pComb3, Capable of Expressing a Phagemid Fab Display Protein The pComb3 phagemid expression vector was used for expressing the synthetic binding site-containing antibodies of this invention. The antibody Fd chain comprising variable ($V_H$) and constant (CH1) domains of the heavy chain were fused with the C-terminal domain of bacteriophage gene III (3) coat protein. Gene III of filamentous phage encodes a 406-residue minor phage coat protein, cpIII (cp3), which is expressed prior to extrusion in the phage assembly process on a bacterial membrane and accumulates on the inner membrane facing into the periplasm of *E. coli*.

The phagemid vector, designated pComb3, allowed for both surface display and soluble forms of Fabs. The vector was designed for the cloning of combinatorial Fab libraries. The Xho I and Spe I sites were provided for cloning complete PCR-amplified heavy chain (Fd) sequences consisting of the region beginning with framework 1 and extending through framework 4. An Aat II restriction site is also present. The presence of the Aat II site allows for the insertion of Xho I/Aat II digests of the PCR products prepared in Example 1 that contain sequences beginning with framework 1 and extending to the end of the CDR3 domain in which the sequences for encoding the synthetic binding sites are located. The insertion of an Xho I/Aat II digest into pC3AP313 results in the fusion of the insert with the framework 4 domain in the pC3AP313 vector. Thus, the insertion results in the in-frame ligation of a complete heavy chain fragment consisting of PCR amplified framework 1 through CDR3 and pC3AP313-retained framework 4. The Sac I and Xba I sites were provided for cloning PCR amplified antibody light chains. The cloning sites were compatible with previously reported mouse and human PCR primers as described by Huse et al., *Science*, 246:1275–1281 (1989) and Persson et al., *Proc. Natl. Acad. Sci., USA*, 88:2432–2436 (1991). The nucleotide sequence of the pelB, a leader sequence for directing the expressed protein to the periplasmic space, was as reported by Huse et al., supra.

The vector also contained a ribosome binding site as described by Shine et al., *Nature*, 254:34 (1975). The sequence of the phagemid vector, pBluescript, which includes ColE1 and F1 origins and a beta-lactamase gene, has been previously described by Short et al., *Nuc. Acids*

Res., 16:7583–7600 (1988) and has the GenBank Accession Number 52330 for the complete sequence. Additional restriction sites, Sal I, Acc I, Hinc II, Cla I, Hind III, Eco RV, Pst I and Sma I, located between the Xho I and Spe I sites of the empty vector were derived from a 51 base pair stuffer fragment of pBluescript as described by Short et al., supra. A nucleotide sequence that encodes a flexible 5 amino acid residue tether sequence that lacks an ordered secondary structure was juxtaposed between the Fab and cp3 nucleotide domains so that interaction in the expressed fusion protein was minimized.

Thus, the resultant combinatorial vector, pComb3, consisted of a DNA molecule having two cassettes to express one fusion protein, Fd/cp3, and one soluble protein, the light chain. The vector also contained nucleotide residue sequences for the following operatively linked elements listed in a 5' to 3' direction: a first cassette consisting of LacZ promoter/operator sequences; a Not I restriction site; a ribosome binding site; a pelB leader; a spacer region; a cloning region bordered by 5' Xho I and 3' Spe I restriction sites; the tether sequence; the sequences encoding bacteriophage cp3 followed by a stop codon; a Nhe I restriction site located between the two cassettes; a second lacZ promoter/operator sequence followed by an expression control ribosome binding site; a pelB leader; a spacer region; a cloning region bordered by 5' Sac I and a 3' Xba I restriction sites followed by expression control stop sequences and a second Not I restriction site.

In the above expression vector, the Fd/cp3 fusion and light chain proteins were placed under the control of separate lac promoter/operator sequences and directed to the periplasmic space by pelB leader sequences for functional assembly on the membrane. Inclusion of the phage F1 intergenic region in the vector allowed for the packaging of single-stranded phagemid with the aid of helper phage. The use of helper phage superinfection allowed for the expression of two forms of cp3. Consequently, normal phage morphogenesis was perturbed by competition between the Fd/cp3 fusion and the native cp3 of the helper phage for incorporation into the virion. The resulting packaged phagemid carried native cp3, which is necessary for infection, and the encoded Fab fusion protein, which is displayed for selection. Fusion with the C-terminal domain was necessitated by the phagemid approach because fusion with the infective N-terminal domain would render the host cell resistant to infection.

The pComb3 expression vector described above forms the basic construct of pC3AP313 and p7EII Fab display phagemid expression vectors used in this invention for the production of human Fab antibodies containing synthetic metal binding sites. The pC3AP313 and p7EII phagemid expression vectors described in Example 1, having the respective ATCC accession numbers 75408 and 75409 as described earlier, are pComb3-based vectors that were originally used to screen for heavy and light chain sequences encoding human Fab antibodies against tetanus toxin.

B. Preparation of Expression Vector Libraries for the Expression of the Phagemid Fab-Display Proteins 1) Phagemid Library Construction In order to obtain expressed human Fab antibodies having both heavy and light chain fragments, phagemid libraries were constructed. The libraries provided for the expression of recombinant human Fab antibodies having heavy and light chains where the synthetic binding sites of this invention are displayed in the heavy chain CDR3. The PCR products resulting from each of the amplification reactions prepared in Example 1 were separately inserted into a phagemid expression vector to prepare phagemid libraries.

As described below, the resultant gel purified heavy chain PCR fragments prepared in Example 1 were digested with the restriction enzymes and separately ligated into the pC3AP313 phagemid expression vector that was similarly digested.

For preparation of phagemid libraries for expressing Fab display proteins that bind to selected metals, the PCR products prepared in Examples 1A and 1B were digested with Xho I and Spe I and ligated with a similarly digested pC3AP313 phagemid expression vector prepared as described in Examples 1 and 2A. The ligation resulted in operatively linking the framework 1 through framework 4 PCR products with the CH1 region present in the pC3AP313 vector.

Phagemid libraries for expressing the Fab display synthetic metal binding sites of this invention from each of the final 5 PCR amplification products produced above were prepared in the following procedure. To form circularized vectors containing the PCR product insert, 640 ng of the digested PCR products were separately admixed with 2 ug of the linearized pC3AP313 phagemid vector and ligation was allowed to proceed overnight at room temperature using 10 units of BRL ligase (Gaithersburg, Md.) in BRL ligase buffer in a reaction volume of 150 ul. Five separate ligation reactions were performed to increase the size of each separate phage library for selecting synthetic metal binding sites in a heavy chain CDR3.

Following the ligation reactions, the circularized DNA was precipitated at −20 C. for two hours by the admixture of 2 ul of 20 mg/ml glycogen, 15 ul of 3M sodium acetate at pH 5.2 and 300 ul of ethanol. DNA was then pelleted by microcentrifugation at 4 C. for 15 minutes. The DNA pellet was washed with cold 70% ethanol and dried under vacuum. The pellet was resuspended in 10 ul of water and transformed by electroporation into 300 ul of *E. coli* XL1-Blue cells to form a phage library. The total yield from the PCR amplification and transformation procedure described herein was approximately $1 \times 10^8$ transformants from each library.

After transformation, to isolate phage on which Fabs displaying synthetic binding sites had been induced for subsequent panning or selection on metal resins as described in Example 3, 3 ml of SOC medium (SOC was prepared by admixture of 20 grams (g) bacto-tryptone, 5 g yeast extract and 0.5 g NaCl in 1 liter of water, adjusting the pH to 7.5 and admixing 20 ml of glucose just before use to induce the expression of the Fd-cpIII and light chain heterodimer) were admixed and the culture was shaken at 220 rpm for 1 hour at 37 C., after which 10 ml of SB were admixed(SB was prepared by admixing 30 g tryptone, 20 g yeast extract, and 10 g Mops buffer per liter with pH adjusted to 7) containing 20 ug/ml carbenicillin and 10 ug/ml tetracycline. The admixture was then shaken at 300 rpm for an additional hour.

This resultant admixture was admixed to 100 ml SB containing 50 ug/ml carbenicillin and 10 ug/ml tetracycline and shaken for 1 hour, after which helper phage VCSM13 ($10^{12}$ pfu) were admixed and the admixture was shaken for an additional 2 hours. After this time, 70 ug/ml kanamycin was admixed and maintained at 30 C. overnight. The lower temperature resulted in better heterodimer incorporation on the surface of the phage. The supernatant was cleared by centrifugation (4000 rpm for 15 minutes in a JA10 rotor at 4 C.). Phage were precipitated by admixture of 4% (w/v) polyethylene glycol 8000 and 3% (w/v) NaCl and maintained on ice for 30 minutes, followed by centrifugation (9000 rpm for 20 minutes in a JA10 rotor at 4 C.). Phage pellets were resuspended in 2 ml of PBS and microcentrifuged for three minutes to pellet debris, transferred to fresh tubes and stored at −20 C. for subsequent screening as described below.

For determining the titering colony forming units (cfu), phage (packaged phagemid) were diluted in SB and 1 ul was used to infect 50 ul of fresh (AOD600=1) *E. coli* XL1-Blue cells grown in SB containing 10 ug/ml tetracycline. Phage and cells were maintained at room temperature for 15 minutes and then directly plated on LB/carbenicillin plates.

3. Selection of the Phagemid Fab-Displayed Synthetic Binding Site Proteins

A. Multiple Pannings of the Phage Library Having Phagemid Fab-Displayed Synthetic Metal Binding Site Proteins The five phage libraries produced in Example 2 having heavy chain fragments with Fab display synthetic binding site regions were panned as described herein on a microtiter plate coated with selected target molecules. The target molecules used in screening for the phagemid-anchored Fab-displayed synthetic metal binding site proteins were magnetite and the metal salts of copper, zinc, lead, cerium and iron (Aldrich Chemicals, Milwaukee, Wis.).

Selection for binding to copper(II) and magnetite utilized all five phage libraries in a competitive fashion such that in the first round of selection libraries were kept separate until the elution step when the binding phage that were eluted were subsequently pooled for amplification and subsequent selections. Sequence analysis of the resulting binding phage revealed that all were derived from libraries E and F, respectively encoding a 16 and 10 amino acid residue CDR3, resulting from the mutagenesis with the oligonucleotides containing the NNK nucleotide triplet degeneracy. Library 7-16 was the original source of semisynthetic fluorescein binding Fabs.

In subsequent selections, only libraries E and F were examined. These libraries retained the aspartic acid residue (D) in the penultimate position (next to last) in the encoded HCDR3 and their success supports the structural significance of this residue within HCDR3. Although the degenerate oligonucleotides used for amplifying the E and F libraries were designed to encode a glycine (G) amino acid residue in the first position of the heavy chain CDR3, in some selected metal binding antibodies, a serine (S) amino acid residue occupied that position. For a listing of the resultant heavy chain CDR3 amino acid sequences, see Section B1 on "Metal Binding Site Polypeptides". The presence of the serine was the result of nonfidelity of the PCR amplification. The antibodies containing a serine in the first position nevertheless were selected by panning as described below against particular metals indicating that the serine was not a deleterious amino acid substitution.

Selection for metal binding using sepharose beads proceeded in an analogous fashion to biopanning described by Parmley et al., *Gene*, 73:305–318 (1988) where the target antigen was immobilized on a microtiter plate. Chelating sepharose (10 mg dry weight) was loaded by suspension in a 10 mM solution of $CUSO_4$, $ZnCl_2$, $CeCl_3$, $FeCl_3$, or $Pb(NO_3)_2$ in water. Excess metal was removed by washing the resin twice with TBS. Phage libraries prepared in Example 2 in 25 mM Mops containing 150 mM NaCl and 1% BSA were applied to the loaded sepharose and maintained at 37 C. with shaking for 2 hours. For the initial selection, beads were washed once with Mops buffered saline. Subsequently, the reacted beads were washed 5 times for rounds 2 and 3 and 10 times for each additional round of selection. Bound phage were eluted once with elution buffer supplemented with 1 mM metal and once with 50 mM EDTA to remove excess metal from the resin. The ten-fold increase in background binding which was presumably due to the increased surface area of the beads necessitated additional rounds of selection, generally 5 to 6 as compared to 3 to 4 for binding to protein antigens and small organic haptens.

Eluted phage were used to infect 2 ml of fresh ($OD_{600}=1$) *E. coli* XL1-Blue cells for 15 minutes at room temperature, after which 10 ml of SB containing 20 ug/ml carbenicillin and 10 ug/ml tetracycline was admixed. Aliquots of (20, 10, and 1/10 ul were removed for plating to determine the number of phage (packaged phagemids) that were eluted from the plate. The culture was shaken for 1 hour at 37 C., after which it was added to 100 ml of SB containing 50 ug/ml carbenicillin and 10 ug/ml tetracycline and shaken for 1 hour. Then helper phage VCSM13 ($10^{12}$ pfu) were added and the culture was shaken for an additional 2 hours. After this time, 70 ug/ml kanamycin was added and the culture was incubated at 37 C. overnight. Phage preparation and further panning were repeated as described above.

Following each round of panning, the percentage yield of phage must be determined, where % yield=(number of phage eluted/number of phage applied)×100.

The final phage output ratio was determined by infecting two ml of logarithmic phase XL1-Blue cells as described above and plating aliquots on selective plates. In the first panning, approximately $10^{11}$ phage were applied to four wells and approximate yields ranged from 5.0 to 8.0×$10^5$ eluted phage. After the fourth panning eluted phage ranged from 1.0×$10^6$ to 1.0×$10^8$ phage. From this procedure, clones were selected from each of the Fab libraries for their ability to bind to their respective selected target proteins. The panned phage surface libraries were then converted into ones expressing soluble Fab-displayed synthetic binding site proteins for further characterization as described in Example 4.

B. Metal Chelate Affinity Chromatography of the Phage Library for Phagemid Fab-Displayed Synthetic Metal Binding Site Proteins For selecting a magnetite-specific Fab displayed synthetic metal binding site protein of this invention, the five phage libraries prepared in Example 2 were applied to affinity columns on which selected metals had been immobilized. For this selection procedure, metal chelate affinity chromatography was performed using Pharmacia HiTrap columns according to manufacturer's instructions (Pharmacia). HiTrap columns are packed with 1 or 5 ml chelating Sepharose High Performance, a newly developed matrix. The columns are made of polyethylene which is biocompatible and non-interactive with biomolecules. The amino acids histidine, cysteine and tryptophan, present in almost every protein, allows for the formation of complexes with many transition metal ions. Thus, the chelating Sepharose High Performance, charged with selected metal ions, selectively retains proteins if the complex-forming amino acid residues are exposed on the protein surface. The Sepharose used in the columns consists of highly cross-linked agarose beads coupled by stable ether groups to iminodiacetic acid via 7-atom spacer arms. The coupling technique ensures both high capacity and performance while minimizing leakage of the iminodiacetic groups.

For selecting magnetite ($Fe_3O_4$)-specific Fab-displaying synthetic binding sites, magnetite was coupled to the chelating Sepharose High Performance following the manufacturer's instructions. The phage preparations from each of the phage libraries prepared in Example 2 were separately applied to the prepared column. To 100 ul of suspended metal complexed resin, 500 ul of $10^{11}$ pfu/ml of phage were added. After allowing the phage-anchored Fabs to immobilize to the metal, the column was washed 5 times with TBS containing 0.1% Tween-20. The metal-specific immobilized phage-anchored Fabs were then eluted with 20 ul of acid (0.1M HCl adjusted to pH 2.2 with glycine, containing BSA at 1 mg/ml). Alternatively, the elution was performed with 200 ul of 50 mM EDTA. Thereafter, the eluted phage were infected into bacteria in order to prepare soluble Fab-displayed binding site proteins.

An alternative method for selection of magnetite-binding Fab antibodies expressed on the surface of phage was performed by applying phage libraries prepared as described above to 1 mg of magnetite in a microfuge tube. The resulting suspension was shaken at 37 C. for 2 hours. Magnetite was pelleted by centrifugation or magnetic force. Magnetite was washed 5 times with TBS-tween in the first 3 rounds of selection and 10 times in the last 3 rounds of selection. Bound phage were eluted with the standard acidic elution buffer. Subsequent steps were performed as described above.

C. Preparation of Soluble Fab-Displayed Metal Binding Site Proteins

In order to further characterize the specificity of the Fab-displayed synthetic binding site proteins expressed on the surface of phage as described above, soluble heterodimers were prepared and analyzed in ELISA assays on target-coated plates and by competitive ELISA with increasing concentrations of soluble competitor as described below.

To prepare soluble Fabs consisting of heavy and light chains (i.e., heterodimers), phagemid DNA from positive clones selected in Examples 3A and 3B above was isolated and digested with Spe I and Nhe I. Digestion with these enzymes produced compatible cohesive ends. The 4.7 kilobase (kb) DNA fragment lacking the gIII portion was gel-purified (0.6% agarose) and self-ligated. Transformation of *E. coli* XL1-Blue afforded the isolation of recombinants lacking the gIII fragment. Clones were examined for removal of the gIII fragment by Xho I/Xba I digestion, which should yield an 1.6 kb fragment. Clones were grown in 100 ml SB containing 50 ug/ml carbenicillin and 20 mM $MgCl_2$ at 37 C. until an $OD_{600}$ of 0.2 was achieved. IPTG (1 mM) was added and the culture grown overnight at 30 C. (growth at 37 C. provides only a light reduction in heterodimer yield). Cells were pelleted by centrifugation at 4000 rpm for 15 minutes in a JA10 rotor at 4 C. Cells were resuspended in 4 ml PBS containing 34 ug/ml phenylmethylsulfonyl fluoride (PMSF) and lysed by sonication on ice (2–4 minutes at 50% duty). Debris was pelleted by centrifugation at 14,000 rpm in a JA20 rotor at 4 C. for 15 minutes. The supernatant was used directly for ELISA analysis and was stored at −20 C. For evaluating a large number of clones, 10 ml cultures provided a sufficient amount of Fab-displayed synthetic binding site proteins for analysis. In this case, sonications were performed in 2 ml of buffer.

The soluble heterodimers prepared above were assayed by ELISA where applicable as described in Example 4.

4. Characterization of Soluble Fabs Containing Metal Binding Sites

A. Determination of Specificity of the Metal Binding Site Proteins

1) ELISA

To assay metal binding specificity of soluble Fabs prepared in Example 3 C, ELISA was performed using a bovine serum albumin-iminodiacetic acid (BSA-IDA) conjugate. A 10 ml solution of 0.1M carbonate buffer at pH 9 was prepared containing 10 mg/ml BSA. A 0.9 mM solution of 1,4-Butanediol diglycidyl ether was added to the BSA-containing solution and allowed to react for 4 hours at 37 C. Iminodiacetic acid, 1.8 mM, neutralized with NaOH and dissolved in 3 ml of 0.1M bicarbonate at pH 9 was then added to the protein containing solution and allowed to react overnight at 37 C. The conjugate was purified by passage over a Pharmacia PD-10 Sephadex column (Pharmacia).

Once the BSA-IDA conjugate was prepared, it was diluted in TBS to 1 ug/ml and was applied to each well of a 96 well ELISA plate. The plate was maintained overnight at 4 C. or for 1 hour at 37 C. to allow for the conjugate to bind to the plastic. The coating solution was then removed and 50 ul of 1% BSA in TBS were applied. After blocking for 30 minutes at 37 C. and removal of the BSA solution, 40 ul of 1 mM EDTA were applied to all wells to chelate preexisting metal ions. After removal of this solution, 40 ul of a 1 mM solution of a metal salt, either $MgCl_2$, $NiCl_2$, $CuCl_2$, $ZnCl_2$, $PbCl_2$, $CeH_2O_3$, and $FeCl_3$, in TBS were separately added to allow for the formation of separate metal-loaded BSA-IDA complexes. Following metal loading, the plate was washed 5 times with purified water, dried and soluble Fab antibodies prepared in Example 3C were separately added to allow for the formation of immunoreaction products. After two hours at 37 C., the plate was washed 10 times with PBS-tween 0.05% to remove unbound soluble Fab. Goat anti-human IgG F(ab')$_2$ coupled to alkaline phosphatase, 40 ul of a 1 ug/ml solution in 1% BSA/TBS were then applied to each well to provide for labeling of the primary immunoreaction product. After 30 minutes at 37 C., the plate was washed 10 times with PBS-tween 0.05%, and the substrate, p-nitrophenyl phosphate, diluted to 0.1% in 10% diethanolamine containing 0.01% $MgCl_2$ at pH 9.8 was added to allow for the detection of the primary immunoreaction products through the labeled reacted secondary antibody. Optical density was measured at 405 nm.

Three Cu(II) selected antibodies, Cu-1, Cu-2 and Cu-11, were prepared in soluble form and purified for use in above ELISA. The results are shown in FIG. 1 where all three Fabs bound Cu(II) loaded BSA-IDA significantly over background. Interestingly, two of these demonstrated a marked preference for nickel (Ni(II)) over all the other metals examined. Each of the three Fabs had unique specificity characteristics, as one might expect from a random selection procedure. These results highlight the diversity which still exists in the metal binding sublibrary. The binding specificity of the Pb(II) and Ce(III) selected Fabs was also confirmed by ELISA.

2) Estimation of the Formation Constant

Formation constants were estimated for Fab Cu-2 binding to nickel-loaded BSA-IDA based on the ELISA results. The BSA-IDA nickel loaded conjugate was prepared as described above. The formation constant was determined by a competition ELISA experiment. A stock solution of $2 \times 10^{-5}$M BSA-IDA was saturated with $NiCl_2$ in TBS. The resultant metal-loaded BSA-IDA solution was then serially diluted to $2 \times 10^{-10}$M. One hundred microliters of each BSA-IDA-Ni solution were pre-maintained with 100 ul of 2 ug/ml of Fab Cu-2 to give final BSA-IDA-Ni concentrations of $10^{-10}$, $10^{-9}$, $10^{-8}$, $10^{-7}$, $10^{-6}$, $5 \times 10^{-6}$ and $10^{-5}$M. Forty microliters of the resultant Cu-2 Fab-Ni-BSA-IDA complexes were then applied in quadruplicate to ELISA wells that had been previously coated with Ni-BSA-IDA. Normal ELISA protocols were then followed as described above. The formation constant was defined as the reciprocal of the concentration of BSA-IDA-metal that reduced $OD_{405}$ to half maximal. Assays were also performed with the addition of EDTA to compete the binding of soluble Fabs containing metal binding sites to metal-loaded substrates.

The formation constant of clone Cu-2 for Ni-BSA-IDA was estimated by competition analysis to be $10^{-7}M$. Previous studies indicate that the formation constant for a single histidine with Cu(II) IDA-polyethylene-glycol is approximately $10^{-3}M$ as described by Suh et al., *Biotechnol. Bio. Engng.*, 33:682–690 (1990). In the instant invention, metal-dependent binding was abolished by addition of EDTA and competed with excess free metal.

B. Sequence Determination of the Binding Site Proteins

Nucleic acid sequencing was performed on double-stranded DNA using Sequenase 1.0 (USB, Cleveland, Ohio) encoding the specific soluble Fab-displayed synthetic metal binding site proteins of this invention characterized above. The amino acid residue sequences and analysis thereof for each of the specific Fab-displayed synthetic binding site proteins specific for magnetite, copper, zinc, lead, cerium, and iron metal salts were listed earlier in specification in Section B1 entitled "Metal Binding Site Polypeptides".

The selected antibodies were either derived from library E or F in which the CDR3 was 16 or 10 amino acid residues in length, respectively, containing an aspattic acid (D) amino acid residue in the penultimate position. Analysis of the sequences of the selected antibodies confirms the success of the selection strategy as shown for example by the Cu(II)-chelating sequences. Based on the knowledge of characterized copper containing protein structures, the expected ligands are His, Met, and Cys. A total of 106 positions within the 11 sequenced Cu(II) selected CDRs were randomized with the NNK-encoded degenerate oligonucleotides designed as described in Example 1B. Histidine was selected at 26 positions, Met at 6, and Cys at 3. The NNK degeneracy provided each of these residues at only one part in 32 in the unselected library. One clone contained an unpaired Cys residue which is a rare feature in antibody CDRs as described by Kabat et al., "Sequences of Proteins of Immunological Interest". 5th Ed., (N.I.H., Washington, D.C., (1991).

By Utilizing IDA immobilized with a 12 atom spacer, selection should not be limited to surface exposed residues. Three clones contained an His at position 102 which is predicted not to be on the surface of the protein as described by Chothia et al., *J. Mol. Biol.*, 196:901–917 (1987). The two His rich clones, Cu-1 and Cu-2, demonstrated a preference for Ni(II)-loaded BSA-IDA while only the Trp rich clone, Cu-11, showed selectivity for Cu(II) as shown in FIG. 1.

Sequences were analyzed for antibodies that were selected for binding to Zn(II), Pb(II), Ce(III), and Fe(III). Zn(II)-selected sequences show the His rich character seen for Cu(II) and one sequence which is identical to that selected with Cu(II). Only one clone was rich in carboxylates. Selection for His, Cys, Asp, and Glu is expected based on studies of natural proteins as described by Vallee et al., *Biochem.*, 29:5647–5659 (1990). The coordinating ligands from sequences selected for binding to Pb(II), Ce(III), and Fe(III) were less obvious. A number of features can however be noted. Pb(II) sequences were rich in Asp and Glu (10% of randomized residues). For comparison, Ce(III), Fe(III), and Cu(II) selected sequences contained these residues at 7%, 4%, and 5%, respectively. The oxygen-containing ligands Ser, Thr, and Tyr constituted 18% of Pb(II) and Ce(III) sequences as compared to 11 and 9% for Fe(III) and Cu(II). The amino acid residues, Ser and Thr, were over-represented at the synthesis level and were present at 3 and 2 parts per 32. Fe(III) sequences were enriched to the 10% level for the sulfur containing residues Cys and Met. Coordination with main chain carbonyl oxygens or amide nitrogens can not be discounted and would not be discernible from sequence analysis.

Thus, within the pool of 20 commonly occurring amino acids almost half were observed to participate in metal ligation within proteins (Asp, Cys, Glu, His, Met, Ser, Thr, Tyr , and Trp). Main chain carbonyl oxygens and amide nitrogens were also be utilized to coordinate metals. Most protein engineering efforts utilize design strategies based on analogy as described by Tainer et al., *Curr. Opin. Biotech.*, 2:582–591 (1991). While such a strategy may be sufficient for the transfer of known metal binding motifs into alternative proteins, it limits ones ability to explore and exploit novel reactivities for most of the periodic table. The ability to selectively sort proteins in vitro for metal ligation has the distinct advantage that it is not limited in scope by natural phylogenies. Furthermore, the approaches of screening for metal binding sites in this invention provides for the ability to generate a variety of ligating groups that provide a multiplicity of coordination numbers and geometries, both of which alter the reactivity of the bound metal.

The efficiency with which the first stage of an iterative approach to achieving catalytic metalloantibodies is demonstrated in this invention. A benefit of such an evolutionary approach, as opposed to a designed template approach, is that sublibraries can be created whose members display a diversity of coordinating residues in a range of potentially useful contexts. The advantage of creating such sublibraries stems from the power of developing selective approaches that allow rare but interesting members to be further selected based on criteria that can be entirely different than those used to create the original library.

5. Deposit of Materials

The following cell lines and plasmids have been deposited on or before Feb. 2, 1993, with the American Type Culture Collection, 1301 Parklawn Drive, Rockville, Md., USA (ATCC):

| Material No. | ATCC Accession |
| --- | --- |
| Plasmid pC3AP313 | ATCC 75408 |
| Plasmid p7EII | ATCC 75409 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The deposits will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the culture deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines and plasmids deposited, since the deposited embodiment is intended as a single illustration of one aspect of the invention and any cell lines or plasmid vectors that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:1:

Ser Arg Arg Ser Arg His His Pro Arg Met Trp Asn Gly Leu Asp Val
1               5                   10                  15

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

Gly Arg Phe Lys Arg Val Arg Asp Arg Trp Val Val Ile Phe Asp Phe
1               5                   10                  15

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:3:

Gly Val Ala Arg Ser Lys Lys Met Arg Gly Leu Trp Arg Leu Asp Val
1               5                   10                  15

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( D ) TOPOLOGY: linear (i i) MOLECULE TYPE: protein (v) FRAGMENT TYPE: internal (x i) SEQUENCE DESCRIPTION: SEQ ID NO:4:

```
Gly  Leu  Ala  Val  Arg  Ser  Lys  Arg  Gly  Arg  Phe  Phe  Leu  Phe  Asp  Val
1                   5                        10                       15
```

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: linear (i i) MOLECULE TYPE: protein (v) FRAGMENT TYPE: internal (x i) SEQUENCE DESCRIPTION: SEQ ID NO:5:

```
Gly  Arg  Val  His  His  His  Ser  Leu  Asp  Val
1                   5                        10
```

(2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: linear (i i) MOLECULE TYPE: protein (v) FRAGMENT TYPE: internal (x i) SEQUENCE DESCRIPTION: SEQ ID NO:6:

```
Ser  Trp  Lys  His  His  Ala  His  Trp  Asp  Val
1                   5                        10
```

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (i i) MOLECULE TYPE: protein (v) FRAGMENT TYPE: internal (x i) SEQUENCE DESCRIPTION: SEQ ID NO:7:

```
Gly  Ser  Trp  Asp  His  Arg  Gly  Cys  Asp  Gly
1                   5                        10
```

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (i i) MOLECULE TYPE: protein (v) FRAGMENT TYPE: internal (x i) SEQUENCE DESCRIPTION: SEQ ID NO:8:

```
Gly  His  His  Met  Tyr  Gly  Gly  Trp  Asp  His
1                   5                        10
```

(2) INFORMATION FOR SEQ ID NO:9:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:9:

```
Gly His Trp Gly Arg His Ser Leu Asp Thr
1               5                   10
```

( 2 ) INFORMATION FOR SEQ ID NO:10:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:10:

```
Gly His Ile Leu His His Gln Leu Asp Leu
1               5                   10
```

( 2 ) INFORMATION FOR SEQ ID NO:11:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:11:

```
Ser Ser Gln Arg Leu Met Leu Gly Asp Asn
1               5                   10
```

( 2 ) INFORMATION FOR SEQ ID NO:12:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:12:

```
Ser His His Gly His His Tyr Leu Asn His
1               5                   10
```

( 2 ) INFORMATION FOR SEQ ID NO:13:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:13:

```
Gly Lys Leu Met Met Ser Trp Cys Arg Asp Thr Glu Gly Cys Asp His
1               5                   10                  15
```

( 2 ) INFORMATION FOR SEQ ID NO:14:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:14:

```
Gly Asp Thr His Arg Gly His Leu Arg His His Leu Pro His Asp Trp
1               5                   10                  15
```

( 2 ) INFORMATION FOR SEQ ID NO:15:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:15:

```
Gly Trp Gly Leu Trp Met Lys Pro Phe Val Trp Arg Ala Trp Asp Met
1               5                   10                  15
```

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:16:

```
Ser His Thr His Ala Leu Pro Leu Asp Phe
1               5                   10
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:17:

```
Gly Arg Val His His His Ser Leu Asp Val
1               5                   10
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:18:

Gly Gln Ser Ser Gly Gly Asp Thr Asp Asp
1               5                   10

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:19:

Gly Gln Trp Thr Pro Arg Gly Asp Asp Phe
1               5                   10

( 2 ) INFORMATION FOR SEQ ID NO:20:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:20:

Gly Arg Cys Cys Pro Ser Ser Cys Asp Glu
1               5                   10

( 2 ) INFORMATION FOR SEQ ID NO:21:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:21:

Gly Pro Ala Lys His Arg His Arg His Val Gly Gln Met His Asp Ser
1               5                   10                  15

( 2 ) INFORMATION FOR SEQ ID NO:22:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:22:

Gly Asn Leu Arg Arg Lys Thr Ser Asp Ile
1               5                   10

( 2 ) INFORMATION FOR SEQ ID NO:23:

( i ) SEQUENCE CHARACTERISTICS:

(A) LENGTH: 10 amino acids
(B) TYPE: amino acid
(D) TOPOLOGY: linear (i i) MOLECULE TYPE: protein (v) FRAGMENT TYPE: internal (x i) SEQUENCE DESCRIPTION: SEQ ID NO:23:

Gly Glu Ser Asp Ser Lys Arg Glu Asp Gly
1               5                   10

(2) INFORMATION FOR SEQ ID NO:24:

(i) SEQUENCE CHARACTERISTICS:
    (A) LENGTH: 10 amino acids
    (B) TYPE: amino acid
    (D) TOPOLOGY: linear (i i) MOLECULE TYPE: protein (v) FRAGMENT TYPE: internal (x i) SEQUENCE DESCRIPTION: SEQ ID NO:24:

Gly Gly Pro Ser Leu Ala Val Gly Asp Trp
1               5                   10

(2) INFORMATION FOR SEQ ID NO:25:

(i) SEQUENCE CHARACTERISTICS:
    (A) LENGTH: 10 amino acids
    (B) TYPE: amino acid
    (D) TOPOLOGY: linear (i i) MOLECULE TYPE: protein (v) FRAGMENT TYPE: internal (x i) SEQUENCE DESCRIPTION: SEQ ID NO:25:

Gly Pro Leu Gln His Thr Tyr Pro Asp Tyr
1               5                   10

(2) INFORMATION FOR SEQ ID NO:26:

(i) SEQUENCE CHARACTERISTICS:
    (A) LENGTH: 16 amino acids
    (B) TYPE: amino acid
    (D) TOPOLOGY: linear (i i) MOLECULE TYPE: protein (v) FRAGMENT TYPE: internal (x i) SEQUENCE DESCRIPTION: SEQ ID NO:26:

Gly Trp Lys Val Thr Ala Glu Asp Ser Thr Glu Gly Leu Phe Asp Leu
1               5                   10                  15

(2) INFORMATION FOR SEQ ID NO:27:

(i) SEQUENCE CHARACTERISTICS:
    (A) LENGTH: 16 amino acids
    (B) TYPE: amino acid
    (D) TOPOLOGY: linear (i i) MOLECULE TYPE: protein (v) FRAGMENT TYPE: internal (x i) SEQUENCE DESCRIPTION: SEQ ID NO:27:

Gly Thr Arg Val Trp Arg Val Cys Gln Trp Asn His Glu Glu Asp Gly
1               5                   10                  15

( 2 ) INFORMATION FOR SEQ ID NO:28:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:28:

```
Gly Glu Trp Trp Cys Ser Phe Ala Met Cys Pro Ala Arg Trp Asp Phe
1               5                   10                  15
```

( 2 ) INFORMATION FOR SEQ ID NO:29:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:29:

```
Gly Asp Thr Ile Phe Gly Val Thr Met Gly Tyr Tyr Ala Met Asp Val
1               5                   10                  15
```

( 2 ) INFORMATION FOR SEQ ID NO:30:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:30:

```
Gly Gln Val Met Gln Glu Leu Gly Asp Ala
1               5                   10
```

( 2 ) INFORMATION FOR SEQ ID NO:31:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:31:

```
Gly Leu Thr Glu Gln Gln Leu Gln Asp Gly
1               5                   10
```

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:32:

Gly Tyr Ser Tyr Ser Val Ser Pro Asp Ala
1               5                   10

( 2 ) INFORMATION FOR SEQ ID NO:33:

( i ) SEQUENCE CHARACTERISTICS:
       ( A ) LENGTH: 10 amino acids
       ( B ) TYPE: amino acid
       ( D ) TOPOLOGY: linear ( i i ) MOLECULE TYPE: protein ( v ) FRAGMENT TYPE: internal ( x i ) SEQUENCE DESCRIPTION: SEQ ID NO:33:

Gly Arg Leu Gly Leu Val Met Thr Asp Glu
1               5                   10

( 2 ) INFORMATION FOR SEQ ID NO:34:

( i ) SEQUENCE CHARACTERISTICS:
       ( A ) LENGTH: 16 amino acids
       ( B ) TYPE: amino acid
       ( D ) TOPOLOGY: linear ( i i ) MOLECULE TYPE: protein ( v ) FRAGMENT TYPE: internal ( x i ) SEQUENCE DESCRIPTION: SEQ ID NO:34:

Ser Thr Trp Pro Gly Arg Gln Arg Leu Gly Gln Ala Leu Ser Asp Ser
1               5                   10                  15

( 2 ) INFORMATION FOR SEQ ID NO:35:

( i ) SEQUENCE CHARACTERISTICS:
       ( A ) LENGTH: 16 amino acids
       ( B ) TYPE: amino acid
       ( D ) TOPOLOGY: linear ( i i ) MOLECULE TYPE: protein ( v ) FRAGMENT TYPE: internal ( x i ) SEQUENCE DESCRIPTION: SEQ ID NO:35:

Gly Tyr Glu Leu Ser Trp Gly Val Asp Gln Gln Glu Trp Trp Asp Ile
1               5                   10                  15

( 2 ) INFORMATION FOR SEQ ID NO:36:

( i ) SEQUENCE CHARACTERISTICS:
       ( A ) LENGTH: 16 amino acids
       ( B ) TYPE: amino acid
       ( D ) TOPOLOGY: linear ( i i ) MOLECULE TYPE: protein ( v ) FRAGMENT TYPE: internal ( x i ) SEQUENCE DESCRIPTION: SEQ ID NO:36:

Gly Pro Val Arg Gly Leu Asp Gln Ser Lys Gly Val Arg Tyr Asp Asn
1               5                   10                  15

( 2 ) INFORMATION FOR SEQ ID NO:37:

( i ) SEQUENCE CHARACTERISTICS:
       ( A ) LENGTH: 16 amino acids
       ( B ) TYPE: amino acid (D) TOPOLOGY: linear (ii) MOLECULE TYPE: protein (v) FRAGMENT TYPE: internal (xi) SEQUENCE DESCRIPTION: SEQ ID NO:37:

```
Gly Leu Ser Gln His Ile Val Ser Glu Thr Gln Ser Ser Gly Asp Leu
1               5                   10                  15
```

(2) INFORMATION FOR SEQ ID NO:38:

(i) SEQUENCE CHARACTERISTICS:
    (A) LENGTH: 16 amino acids
    (B) TYPE: amino acid
    (D) TOPOLOGY: linear (ii) MOLECULE TYPE: protein (v) FRAGMENT TYPE: internal (xi) SEQUENCE DESCRIPTION: SEQ ID NO:38:

```
Gly Leu Glu Ser Leu Lys Val Leu Gly Val Gln Leu Gly Gly Asp Leu
1               5                   10                  15
```

(2) INFORMATION FOR SEQ ID NO:39:

(i) SEQUENCE CHARACTERISTICS:
    (A) LENGTH: 16 amino acids
    (B) TYPE: amino acid
    (D) TOPOLOGY: linear (ii) MOLECULE TYPE: protein (v) FRAGMENT TYPE: internal (xi) SEQUENCE DESCRIPTION: SEQ ID NO:39:

```
Gly Asn Met Ile Leu Gly Gly Pro Gly Cys Trp Ser Ser Ala Asp Ile
1               5                   10                  15
```

(2) INFORMATION FOR SEQ ID NO:40:

(i) SEQUENCE CHARACTERISTICS:
    (A) LENGTH: 16 amino acids
    (B) TYPE: amino acid
    (D) TOPOLOGY: linear (ii) MOLECULE TYPE: protein (v) FRAGMENT TYPE: internal (xi) SEQUENCE DESCRIPTION: SEQ ID NO:40:

```
Gly Cys Trp Asn Val Gln Arg Leu Val Val Tyr His Pro Pro Asp Gly
1               5                   10                  15
```

(2) INFORMATION FOR SEQ ID NO:41:

(i) SEQUENCE CHARACTERISTICS:
    (A) LENGTH: 16 amino acids
    (B) TYPE: amino acid
    (D) TOPOLOGY: linear (ii) MOLECULE TYPE: protein (v) FRAGMENT TYPE: internal (xi) SEQUENCE DESCRIPTION: SEQ ID NO:41:

```
Gly Phe Glu Val Thr Cys Ser Trp Phe Gly His Trp Gly Arg Asp Ser
1               5                   10                  15
```

( 2 ) INFORMATION FOR SEQ ID NO:42:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:42:

```
Ser Ala Ser Met Arg Ser Ala Ile Gly Leu Trp Arg Thr Met Asp Tyr
 1               5                  10                  15
```

( 2 ) INFORMATION FOR SEQ ID NO:43:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:43:

```
Gly Asp Arg Glu Ile Phe His Met Gln Trp Pro Leu Arg Val Asp Val
 1               5                  10                  15
```

( 2 ) INFORMATION FOR SEQ ID NO:44:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:44:

```
Ser Gln Asn Pro Gln Gln Val Cys Gly Val Arg Cys Gly Gln Asp Lys
 1               5                  10                  15
```

( 2 ) INFORMATION FOR SEQ ID NO:45:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:45:

```
Gly Asn Arg Leu Ser Ser Gly His Leu Leu Lys Gln Gly Gln Asp Gly
 1               5                  10                  15
```

( 2 ) INFORMATION FOR SEQ ID NO:46:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:46:

```
Gly Gly Ser Asp Trp Gln Ile Gly Ala Cys Cys Arg Glu Asp Asp Leu
1               5                   10                  15
```

( 2 ) INFORMATION FOR SEQ ID NO:47:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:47:

```
Gly Met Val Ser Met Met Gly Gln Ser Arg Pro Thr Gln Cys Asp Cys
1               5                   10                  15
```

( 2 ) INFORMATION FOR SEQ ID NO:48:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:48:

```
Gly Val Ile Lys Trp Ile Arg Arg Trp Val Arg Thr Ala Arg Asp Val
1               5                   10                  15
```

( 2 ) INFORMATION FOR SEQ ID NO:49:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:49:

```
Gly Trp Phe Trp Arg Leu Leu Pro Thr Pro Arg Ala Pro Ser Asp Val
1               5                   10                  15
```

( 2 ) INFORMATION FOR SEQ ID NO:50:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:50:

```
GTGTATTATT GTGCGAGANN SNNSNNSNNS NNSTGGGGCC AAGGGACCAC G          51
```

( 2 ) INFORMATION FOR SEQ ID NO:51:

( i ) SEQUENCE CHARACTERISTICS:
        ( A ) LENGTH: 66 base pairs
        ( B ) TYPE: nucleic acid ( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:51:

GTGTATTATT GTGCGAGANN SNNSNNSNNS NNSNNSNNSN NSNNSNNSTG GGGCCAAGGG     60

ACCACG     66

( 2 ) INFORMATION FOR SEQ ID NO:52:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:52:

GCCGTGTATT ACTGTGCGAG AGGTNNKNNK NNKNNKNNKN NKNNKGACNN KTGGGGCCAA     60

GGGACCACGG TC     72

( 2 ) INFORMATION FOR SEQ ID NO:53:

( i ) SEQUENCE CHARACTERISTICS:
( A ) LENGTH: 90 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:53:

GCCGTGTATT ACTGTGCGAG AGGTNNKNNK NNKNNKNNKN NKNNKNNKNN KNNKNNKNNK     60

NNKGACNNKT GGGGCCAAGG GACCACGGTC     90

( 2 ) INFORMATION FOR SEQ ID NO:54:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:54:

CGGGTGTATT ACTGTGCGAG ANNKNNKNNK GACNNKTGGG CCAAGGGAC CACGGTC     57

( 2 ) INFORMATION FOR SEQ ID NO:55:

( i ) SEQUENCE CHARACTERISTICS:

(A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:55:

GCAATTAACC CTCACTAAAG GG    22

(2) INFORMATION FOR SEQ ID NO:56:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:56:

TCTCGCACAA TAATACACGG C    21

(2) INFORMATION FOR SEQ ID NO:57:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:57:

GCATGTACTA GTTTTGTCAC AAGATTTGGG    30

(2) INFORMATION FOR SEQ ID NO:58:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:58:

TCTCGCACAG TAATACACGG CCGT    24

(2) INFORMATION FOR SEQ ID NO:59:

(i) SEQUENCE CHARACTERISTICS:
            (A) LENGTH: 5 amino acids
            (B) TYPE: amino acid
            (D) TOPOLOGY: linear (i i) MOLECULE TYPE: protein (v) FRAGMENT TYPE: internal (x i) SEQUENCE DESCRIPTION: SEQ ID NO:59:

```
Xaa  Xaa  Xaa  Asp  Xaa
1                  5
```

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:60:

```
TTGATATTCA  CAAACGAATG  G                                    21
```

(2) INFORMATION FOR SEQ ID NO:61:

(i) SEQUENCE CHARACTERISTICS:
        (A) LENGTH: 10 amino acids
        (B) TYPE: amino acid
        (D) TOPOLOGY: linear (i i) MOLECULE TYPE: protein (v) FRAGMENT TYPE: internal (x i) SEQUENCE DESCRIPTION: SEQ ID NO:61:

```
Gly  Xaa  Xaa  Xaa  Xaa  Xaa  Xaa  Xaa  Asp  Xaa
1                   5                        10
```

(2) INFORMATION FOR SEQ ID NO:62:

(i) SEQUENCE CHARACTERISTICS:
        (A) LENGTH: 16 amino acids
        (B) TYPE: amino acid
        (D) TOPOLOGY: linear (i i) MOLECULE TYPE: protein (v) FRAGMENT TYPE: internal (x i) SEQUENCE DESCRIPTION: SEQ ID NO:62:

```
Gly  Xaa  Xaa  Xaa  Xaa  Xaa  Xaa  Xaa  Xaa  Xaa  Xaa  Xaa  Xaa  Xaa  Asp  Xaa
1                   5                        10                       15
```

(2) INFORMATION FOR SEQ ID NO:63:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: repeat_region
        (B) LOCATION: 19..21

(D) OTHER INFORMATION: /rpt_type= "direct"
/ label= NNS
/ note= "The NNS triplet degeneracy is repeated depending on the desired length of the CDR."

(x i) SEQUENCE DESCRIPTION: SEQ ID NO:63:

GTGTATTATT GTGCGAGANN STGGGGCCAA GGGACCACG    39

(2) INFORMATION FOR SEQ ID NO:64:

(i) SEQUENCE CHARACTERISTICS:
  (A) LENGTH: 54 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (ix) FEATURE:
  (A) NAME/KEY: repeat_region
  (B) LOCATION: 25..27
  (D) OTHER INFORMATION: /rpt_type= "direct"
      / label= NNS
      / note= "The NNK triplet degeneracy is repeated depending on the desired length of the CDR."

(x i) SEQUENCE DESCRIPTION: SEQ ID NO:64:

GCCGTGTATT ACTGTGCGAG AGGTNNKGAC NNKTGGGGCC AAGGGACCAC GGTC    54

(2) INFORMATION FOR SEQ ID NO:65:

(i) SEQUENCE CHARACTERISTICS:
  (A) LENGTH: 51 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (ix) FEATURE:
  (A) NAME/KEY: repeat_region
  (B) LOCATION: 22..24
  (D) OTHER INFORMATION: /rpt_type= "direct"
      / label= NNS
      / note= "The NNK triplet degeneracy is repeated depending on the desired length of the CDR."

(x i) SEQUENCE DESCRIPTION: SEQ ID NO:65:

CGGGTGTATT ACTGTGCGAG ANNKGACNNK TGGGGCCAAG GGACCACGGT C    51

What is claimed is:

1. In a method for producing a metal binding site in a polypeptide capable of binding a preselected metal ion-containing molecule, the step of inducing mutagenesis of a complementarity determining region (CDR) of an immunoglobulin heavy or light chain gene, wherein said mutagenesis introduces a metal binding site, by amplifying the CDR of said gene by a primer extension reaction using a primer oligonucleotide, said oligonucleotide comprising:

a) a 3' terminus and a 5' terminus comprising;

b) a nucleotide sequence at said 3' terminus complementary to a first framework region of said heavy or light chain immunoglobulin gene;

c) a nucleotide sequence at said 5' terminus complementary to a second framework region of said heavy or light chain immunoglobulin gene; and d) a nucleotide sequence between said 3' terminus and 5' terminus according to the formula;

[NNS]$_a$, wherein N is independently any nucleotide, S is G or C, and a is from 3 to about 50, and said 3' and 5' terminal nucleotide sequences having a length of about 6 to 50 nucleotides, and sequences complementary thereto.

2. The method of claim 1 wherein said immunoglobulin is a human immunoglobulin.

3. The method of claim 1 wherein said CDR is CDR3.

4. The method of claim 1 that further comprises the steps of:
   a) isolating the amplified CDR to form mutagenized immunoglobulin genes;
   b) expressing the isolated mutagenized immunoglobulin genes; and
   c) selecting species of the expressed mutagenized immunoglobulin genes for the ability to bind a preselected metal ion-containing molecule.

5. The method of claim 1 wherein said oligonucleotide has the formula: 5'-GTGTATTATTGTGCGAGA[NNS]$_a$ TGGGGCCAAGGGACCACG-3' (SEQ ID NO 63), and complementary sequences thereto.

6. The method of claim 5 wherein a in [NNS]$_a$ is 5.

7. The method of claim 5 wherein a in [NNS]$_a$ is 10.

8. The method of claim 1 wherein said preselected metal ion-containing molecule is selected from the group consisting of magnetite, copper(II), zinc(II), lead(II), cerium(III), and iron(III).

9. In a method for producing a metal binding site in a polypeptide capable of binding a preselected metal ion-containing molecule, the step of inducing mutagenesis of a complementarity determining region (CDR) of an immunoglobulin heavy or light chain gene by amplifying the CDR of said gene by a primer extension reaction using a primer oligonucleotide, said oligonucleotide comprising:
   a) a 3' terminus and a 5' terminus
   b) a nucleotide sequence at said 3' terminus complementary to a first framework region of said heavy or light chain immunoglobulin gene;
   c) a nucleotide sequence at said 5' terminus complementary to a second framework region of said heavy or light chain immunoglobulin gene; and
   d) a nucleotide sequence between 3' terminus and 5' terminus according to the formula:

-X-[NNK]$_a$-X-[NNK]-X-, wherein N is independently any nucleotide, K is G or T, X is a trinucleotide encoding a native amino acid residue coded by said immunoglobulin gene and a is from 3 to about 50, and said 3' and 5' terminal nucleotide sequences having a length of about 6 to 50 nucleotides, and sequences complementary hereto.

10. The method of claim 9 wherein said immunoglobulin is a human immunoglobulin.

11. The method of claim 9 wherein said CDR is CDR3.

12. The method of claim 9 that further comprises the steps of:
   a) isolating the amplified CDR to form mutagenized immunoglobulin genes;
   b) expressing the isolated mutagenized immunoglobulin genes; and
   c) selecting species of the expressed mutagenized immunoglobulin genes for the ability to bind a preselected metal ion-containing molecule.

13. The method of claim 9 wherein said oligonucleotide has the formula: 5'-GCCGTGTATTACTGTGCGAGAGGT [NNK]$_a$GACNNKTGGGGCCAAGGGACCACGGTC-3' (SEQ ID NO 64).

14. The method of claim 13 wherein a in [NNS]$_a$ is 7.

15. The method of claim wherein a in [NNS]$_a$ is 13.

16. The method of claim 9 wherein said oligonucleotide has the formula: 5'-CGGGTGTATTACTGTGCGAGA [NNK]$_a$GACNNKTGGGGCCAAGGGACCACGGTC-3' (SEQ ID NO 65).

17. The method of claim 16 wherein a in [NNS]$_a$ is 3.

18. The method of claim 9 wherein said preselected metal ion-containing molecule is selected from the group consisting of magnetite, copper(II), zinc(II), lead(II), cerium(III), and iron(III).

* * * * *